US011179500B2

(12) United States Patent
Boden et al.

(10) Patent No.: US 11,179,500 B2
(45) Date of Patent: Nov. 23, 2021

(54) JAB1 INHIBITORY COMPOSITIONS FOR OSSIFICATION AND METHODS RELATED THERETO

(75) Inventors: Scott D. Boden, Atlanta, GA (US); Sreedhara Sangadala, Dallas, GA (US)

(73) Assignees: EMORY UNIVERSITY, Altanta, GA (US); The United States Department of Veterans Affairs, Washington, DC (US)

( * ) Notice: Subject to any disclaimer, the term of this patent is extended or adjusted under 35 U.S.C. 154(b) by 1304 days.

(21) Appl. No.: 13/980,593

(22) PCT Filed: Feb. 23, 2012

(86) PCT No.: PCT/US2012/026248
§ 371 (c)(1),
(2), (4) Date: Sep. 3, 2013

(87) PCT Pub. No.: WO2012/116137
PCT Pub. Date: Aug. 30, 2012

(65) Prior Publication Data
US 2013/0344165 A1    Dec. 26, 2013

Related U.S. Application Data

(60) Provisional application No. 61/446,198, filed on Feb. 24, 2011.

(51) Int. Cl.
*A61L 27/54* (2006.01)
*A61L 27/46* (2006.01)

(52) U.S. Cl.
CPC ............. *A61L 27/54* (2013.01); *A61L 27/46* (2013.01); *A61L 2300/414* (2013.01); *A61L 2430/02* (2013.01); *A61L 2430/06* (2013.01)

(58) Field of Classification Search
CPC .... A61L 27/54; A61L 27/46; A61L 2300/414; A61L 2430/02; A61L 2430/06
See application file for complete search history.

(56) References Cited

U.S. PATENT DOCUMENTS

| | | | | |
|---|---|---|---|---|
| 6,037,519 | A | * | 3/2000 | McKay ................. 623/16.11 |
| 6,124,374 | A | * | 9/2000 | Kolias ................. A61K 6/0026 106/35 |
| 6,309,670 | B1 | * | 10/2001 | Heidaran ............... A61L 27/24 424/484 |

(Continued)

FOREIGN PATENT DOCUMENTS

| | | | | |
|---|---|---|---|---|
| EP | 0 326 330 | * | 8/1989 | ........ C07D 215/22 |
| EP | 12748998 | | 10/2014 | |
| WO | 2010044753 | | 4/2010 | |

OTHER PUBLICATIONS

Kubo et al.: Synthesis and structure-activity relationship for new series of 4-phenoxyquinoline derivative as specific inhibitors of platelet-derived growth factor receptor tyrosine kinase, Bioorganic & Medicinal Chemistry, 11, 2003, 5117-5133.*

(Continued)

*Primary Examiner* — Hong Yu
(74) *Attorney, Agent, or Firm* — Emory Patent Group

(57) ABSTRACT

This disclosure relates to compounds and compositions for forming bone and methods related thereto. In certain embodiments, the disclosure relates to methods of forming bone comprising implanting a bone graft composition comprising a growth factor such as BMP in a subject at a site of desired bone growth or enhancement in combination with a JAB1 blocker.

20 Claims, 7 Drawing Sheets

Specification includes a Sequence Listing.

(56) References Cited

U.S. PATENT DOCUMENTS

| | | | |
|---|---|---|---|
| 2002/0193883 A1 | 12/2002 | Wironen | |
| 2003/0144178 A1 | 7/2003 | Uckun | |
| 2003/0149437 A1* | 8/2003 | Livne et al. | 606/76 |
| 2006/0009460 A1* | 1/2006 | Dickson, Jr. | A61K 31/4709 514/252.02 |
| 2009/0054313 A9 | 2/2009 | Marx et al. | |
| 2009/0291113 A1* | 11/2009 | Soula | A61L 24/10 424/423 |
| 2010/0029675 A1 | 2/2010 | Hwang | |
| 2010/0068204 A1 | 3/2010 | Tsou | |

OTHER PUBLICATIONS

Paniagua et al.: Tyrosine kinases in inflammatory dermatologic disease, Journal of American Academy of Dermatology, Aug. 2011, 65(2), 389-403.*

Matrix: retrieved from internet: https://www.merriam-webster.com/dictionary/matrix. Retrieved on Apr. 19, 2018.*

Nishitoh, et al.: Identification of Type I and Type II Serine/Threonine Kinase Receptors for Growth/Differentiation Factor-5, J. Biol. Chem. 271:21345-21352, 1996.*

Ioannidis, et al., (2010). "Discovery of 5-Chloro-N2-[(1S)-1-(5-fluoropyrimidin-2-yl)ethyl]-N4-(5-methyl-1H-pyrazol-3-yl)pyrimidine-2,4-diamine (AZD1480) as a Novel Inhibitor of the Jak/Stat Pathway." Journal of Medicinal Chemistry, 54(1): 262-276.

Haag & Aigner Jun Activation Domain—Binding Protein 1 Binds Smad5 and Inhibits Bone Morphogenetic Protein Signaling Arthritis & Rheumatism vol. 54, No. 12, 2006, pp. 3878-3884.

Wan et al. Jab1 antagonizes TGF-beta signaling by inducing Smad4 degradation,EMBO Rep. 2002, 3(2):171-6.

Zheng et al (2005) Structure-activity relationship of triazafluorenone derivatives as potent and selective mGluR1 antagonists. J Med Chem, 48: 7374-7388.

Beukers et al. New, non-adenosine, high-potency agonists for the human adenosine A2B receptor with an improved selectivity profile compared to the reference agonist N-ethylcarboxamidoadenosine. J Med Chem. Jul. 15, 2004;47(15):3707-9.

Golub et al. "The role of alkaline phosphatase in mineralization" Current Opinion in Orthopaedics, 2007; 18(5):444-448.

Liu et al. "Activation of c-Jun NH2-Terminal Kinase 1 Increases Cellular Responsiveness to BMP-2 and Decreases Binding of Inhibitory Smad6 to the Type 1 BMP Receptor" Journal of Bone and Mineral Research, May 2011; 26(5):1122-1132.

* cited by examiner

SEQUENCE LISTING

```
<160> NUMBER OF SEQ ID NOS: 6

<210> SEQ ID NO 1
<211> LENGTH: 396
<212> TYPE: PRT
<213> ORGANISM: Homo sapiens

<400> SEQUENCE: 1

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
```

165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 2
<211> LENGTH: 23
<212> TYPE: PRT
<213> ORGANISM: Homo sapiens

<400> SEQUENCE: 2

Lys Ile Pro Lys Ala Ser Ser Val Pro Thr Glu Leu Ser Ala Ile Ser
1               5                   10                  15

Thr Leu Tyr Leu Asp Asp Asp
            20

<210> SEQ ID NO 3
<211> LENGTH: 28
<212> TYPE: PRT
<213> ORGANISM: Homo sapiens

<400> SEQUENCE: 3

Cys Cys Cys Cys Asp Asp Asp Ser Lys Ile Pro Lys Ala Ser Ser Val
1               5                   10                  15

Pro Thr Glu Leu Ser Ala Ile Ser Thr Leu Tyr Leu
            20                  25

<210> SEQ ID NO 4
<211> LENGTH: 30
<212> TYPE: PRT
<213> ORGANISM: Homo sapiens
<220> FEATURE:
<221> NAME/KEY: MOD_RES

```
<222> LOCATION: (1)..(1)
<223> OTHER INFORMATION: ACETYLATION at this location
<220> FEATURE:
<221> NAME/KEY: MISC_FEATURE
<222> LOCATION: (1)..(1)
<223> OTHER INFORMATION: C16H31O-NH

<400> SEQUENCE: 4

Ala Ala Cys Cys Cys Cys Gly Gly Gly Ser Lys Ile Pro Lys Ala Ser
1               5                   10                  15

Ser Val Pro Thr Glu Leu Ser Ala Ile Ser Thr Leu Tyr Leu
            20                  25                  30

<210> SEQ ID NO 5
<211> LENGTH: 431
<212> TYPE: PRT
<213> ORGANISM: Homo sapiens

<400> SEQUENCE: 5

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300
```

```
Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
            325                 330                 335

Val Ser Phe Arg Asp Leu Gly Trp Gln Asp Trp Ile Ile Ala Pro Glu
        340                 345                 350

Gly Tyr Ala Ala Tyr Tyr Cys Glu Gly Glu Cys Ala Phe Pro Leu Asn
    355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
            405                 410                 415

Leu Lys Lys Tyr Arg Asn Asn Val Val Arg Ala Cys Gly Cys His
            420                 425                 430

<210> SEQ ID NO 6
<211> LENGTH: 334
<212> TYPE: PRT
<213> ORGANISM: Homo sapiens

<400> SEQUENCE: 6

Met Ala Ala Ser Gly Ser Gly Met Ala Gln Lys Thr Trp Glu Leu Ala
1               5                   10                  15

Asn Asn Met Gln Glu Ala Gln Ser Ile Asp Glu Ile Tyr Lys Tyr Asp
            20                  25                  30

Lys Lys Gln Gln Gln Glu Ile Leu Ala Ala Lys Pro Trp Thr Lys Asp
        35                  40                  45

His His Tyr Phe Lys Tyr Cys Lys Ile Ser Ala Leu Ala Leu Leu Lys
    50                  55                  60

Met Val Met His Ala Arg Ser Gly Gly Asn Leu Glu Val Met Gly Leu
65                  70                  75                  80

Met Leu Gly Lys Val Asp Gly Glu Thr Met Ile Ile Met Asp Ser Phe
                85                  90                  95

Ala Leu Pro Val Glu Gly Thr Glu Thr Arg Val Asn Ala Gln Ala Ala
            100                 105                 110

Ala Tyr Glu Tyr Met Ala Ala Tyr Ile Glu Asn Ala Lys Gln Val Gly
        115                 120                 125

Arg Leu Glu Asn Ala Ile Gly Trp Tyr His Ser His Pro Gly Tyr Gly
    130                 135                 140

Cys Trp Leu Ser Gly Ile Asp Val Ser Thr Gln Met Leu Asn Gln Gln
145                 150                 155                 160

Phe Gln Glu Pro Phe Val Ala Val Ile Asp Pro Thr Arg Thr Ile
                165                 170                 175

Ser Ala Gly Lys Val Asn Leu Gly Ala Phe Arg Thr Tyr Pro Lys Gly
            180                 185                 190

Tyr Lys Pro Pro Asp Glu Gly Pro Ser Glu Tyr Gln Thr Ile Pro Leu
        195                 200                 205

Asn Lys Ile Glu Asp Phe Gly Val His Cys Lys Gln Tyr Tyr Ala Leu
    210                 215                 220

Glu Val Ser Tyr Phe Lys Ser Ser Leu Asp Arg Lys Leu Leu Glu Leu
225                 230                 235                 240

Leu Trp Asn Lys Tyr Trp Val Asn Thr Leu Ser Ser Ser Ser Leu Leu
```

-continued

```
                245                 250                 255
Thr Asn Ala Asp Tyr Thr Thr Gly Gln Val Phe Asp Leu Ser Glu Lys
                260                 265                 270

Leu Glu Gln Ser Glu Ala Gln Leu Gly Arg Gly Ser Phe Met Leu Gly
            275                 280                 285

Leu Glu Thr His Asp Arg Lys Ser Glu Asp Lys Leu Ala Lys Ala Thr
            290                 295                 300

Arg Asp Ser Cys Lys Thr Thr Ile Glu Ala Ile His Gly Leu Met Ser
305                 310                 315                 320

Gln Val Ile Lys Asp Lys Leu Phe Asn Gln Ile Asn Ile Ser
                325                 330
```

JAB1 INHIBITORY COMPOSITIONS FOR OSSIFICATION AND METHODS RELATED THERETO

CROSS REFERENCE TO RELATED APPLICATIONS

This application claim priority to U.S. provisional application No. 61/446,198 filed Feb. 24, 2011, hereby incorporated by reference in its entirety.

BACKGROUND

Bone grafting is typically performed for spinal fusions, after cancerous bone removal, and in certain operations, e.g., plastic surgery. The iliac crest is often used as a donor site for autologous grafts. Complications collecting bone from the iliac crest include pain, nerve damage, hematoma and wound complications, avulsion of the anterior superior iliac spine (ASIS), hematoma, herniation of the abdominal cavity contents, and cosmetic deformity. Thus, it is desirable to develop materials and methods of forming bone that do not require harvesting bone from remote sites of the patient.

Synthetic bone grafts typically include a matrix that holds minerals and other salts. Natural bone has an intracellular matrix mainly composed of type I collagen, and some synthetic bone grafts include a collagen matrix. Synthetic bone grafts typically contain bone growths factors such as bone morphogenetic proteins (BMPs) because of their ability to induce ossification in the matrix material. Recombinant human BMP-2 has been approved by the FDA in synthetic bone grafts such as INFUSE™. INFUSE™ is approved for open tibial shaft fractures, lumbar interbody fusion, and sinus and alveolar ridge augmentations. However, the high cost and need for high concentrations of BMP-2 for treatment creates a barrier for routine clinical use. Thus, there is a need to identify additional compositions that may substitute or complement the use of BMPs in treating bone-related conditions.

Transcriptional regulator JAB1 is an inhibitor of BMP signaling in chondrocytes. It has been implicated in chrodrocyte differentiation. See Haag & Aigner, Arthritis & Rheumatism, 2006, 54(12):3878-3884.

SUMMARY

This disclosure relates to compounds and compositions for ossification and methods related thereto. In certain embodiments, it is an object of the disclosure to provide therapeutics that modulate the effects of JAB1 have the potential to either replace BMPs as a strategy to induce bone formation or serve as a method to enhance the efficacy of BMPs. In certain embodiments, the disclosure relates to methods of forming bone comprising implanting a bone graft composition comprising a growth factor such as BMP in a subject at a site of desired bone growth or enhancement in combination with a JAB1 blocker by including the JAB1 blocker in the bone graft composition and/or by administering a pharmaceutical composition comprising the JAB1 blocker to the subject. The JAB1 blocker could be used by itself without exogenous BMP.

In certain embodiments, the disclosure relates to methods of forming bone or cartilage comprising implanting a bone graft composition comprising a JAB1 blocker optionally comprising a growth factor in a subject at a site of desired bone or cartilage growth.

In certain embodiments, the disclosure relates to methods of forming bone comprising a) implanting a bone graft composition optionally comprising a JAB1 blocker and optionally comprising a growth factor in a subject at a site of desired bone or cartilage growth and b) administering a pharmaceutical composition comprising a JAB1 blocker to the subject.

In certain embodiments, the disclosure relates to uses of compounds disclosed herein and derivatives or salts thereof for cartilage regeneration e.g., between intervertebral disc and articular, jaw, elbow, knee, ankle, wrist, and hip joints. Methods contemplate oral administration, intravenous administration, or direct injection at the desired site(s) of the subject.

In certain embodiments, the JAB1 blocker is a compound disclosed herein such as, a quinoline derivative, 4-(phenoxy)-quinoline derivative, N-phenylquinolin-4-amine derivative, $N^2$-(phenyl)-$N^4$-(phenyl)pyrimidine-2,4-diamine derivative, 3-(benzylidene)indolin-2-one derivatives, 2-((phenylamino)methylene)malononitrile derivative, 2-benzylidenemalononitrile derivative, N'-benzylidene-2-naphthohydrazide derivative, 3-((indol-3-yl)methylene)indolin-2-one derivative, or salts thereof. In certain embodiments, the derivatives comprise one or more substituents. A typical 4-(phenoxy)-quinoline derivative is 4-(4-bromo-3-methylphenoxy)-6,7-dimethoxyquinoline. A typical $N^2$-(phenyl)-$N^4$-(phenyl)pyrimidine-2,4-diamine derivative is $N^2$-(3,5-dimethoxyphenyl)-$N^4$-(4-fluorophenyl)pyrimidine-2,4-diamine. A typical 3-(benzylidene)indolin-2-one derivative is 6-chloro-3-(2,4,6-trimethoxybenzylidene)indolin-2-one. A typical 2-((phenylamino)methylene)malononitrile derivative is 2-(((4-bromophenyl)amino)methylene)malononitrile. A typical 2-benzylidenemalononitrile derivative is 2-(3,4-dimethoxybenzylidene)malononitrile and 2-(2-hydroxy-5-methylbenzylidene) malononitrile. A typical N'-benzylidene-2-naphthohydrazide derivative is N'-(3,5-dichloro-4-hydroxybenzylidene)-3-hydroxy-2-naphthohydrazide. A typical 3-((indol-3-yl)methylene)indolin-2-one derivative is 3-((indol-3-yl)methylene)-7-fluoroindolin-2-one. A typical N-phenylquinolin-4-amine derivative is N-(3-chlorophenyl)-6,7-dimethoxyquinolin-4-amine.

In some embodiments, the disclosure relates to a bone graft compositions comprising a compound disclosed herein, such quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof, and a graft matrix. Typically, the matrix comprises a collagen sponge and/or a compression resistant type I collagen and calcium phosphates. In other embodiments, the matrix is a hydrogel. In certain embodiments, the quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof are covalently linked to a graft matrix.

Within certain embodiments, it is contemplated that the compounds disclosed herein may be linked, e.g., covalently bound to the matrix, carrier, or scaffold such that a bone morphogenetic protein would be resistant to the degrading effects of JAB1 in order to reduce or eliminate BMP in the graft composition to induce bone growth because JAB1 degrades intracellular proteins in BMP signaling.

In certain embodiments, the bone graft compositions further comprise a bone morphogenetic protein and/or another growth factor. Typically, the bone morphogenetic protein is BMP-2 or BMP-7. In certain embodiments, the graft composition comprises calcium phosphates and/or bone granules, hydroxyapatite and/or beta-tricalcium phosphate, alpha-tricalcium phosphate, polysaccharides or combinations thereof. Crushed bone granules, typically obtained from the subject, are optionally added to the graft composition.

In some embodiments, the disclosure relates to kits comprising a graft composition, a compound disclosed herein, such as quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof, thereof and a graft matrix. In certain embodiments, the kits further comprise a bone morphogenetic protein and/or another growth factor. In certain embodiments, the kits further comprise a transfer device, such as a syringe or pipette.

Compositions comprising JAB1 blockers may be dripped into the graft matrix, carrier, or scaffold optionally in combination with other osteogenic agents such as a mesenchymal stem cell, a bone morphogenetic protein, other bone growth factors and/or a statin.

In some embodiments, the disclosure relates to methods of generating BMP-mediated osteoblasts comprising administering an effective amount of compound(s) disclosed herein to cells capable of osteoblastic differentiation, such as mesenchymal stem cells and pre-osteoblastic cells.

In some embodiments, the disclosure relates to methods of forming bone comprising implanting a graft composition comprising a compound disclosed herein, such quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof, thereof in a subject under conditions such that bone forms in the graft. Typically, the subject has a void in the bony structure wherein the graft composition is implanted in the void. In certain embodiments, the void is in a bone selected from an extremity, maxilla, mandible, pelvis, spine and/or cranium. In certain embodiments, the void is a result of surgical removal of bone. In certain embodiments, the void is between bone and an implanted medical device. In another embodiment, the method further comprises the step of securing movement of bone structure with a fixation system, and removing the system after bone forms in the implanted graft.

In some embodiments, the disclosure relates to methods of performing spinal fusion comprising implanting a bone graft composition comprising a compound disclosed herein, such as quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof, configured to grow bone between two vertebrae of a subject. In certain embodiments, the composition further comprises a bone morphogenetic protein and/or another growth factor. In a typical embodiment, the subject is diagnosed with degenerative disc disease or has symptoms of back pain.

In some embodiments, the disclosure relates to methods of inserting a prosthetic device or anchor comprising, exposing the bone; implanting a graft composition comprising compounds disclosed herein, such as quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof, in contact with the bone. In certain embodiments, one implants the prosthetic device or anchor in the graft composition. In certain embodiments, the composition further comprises a bone morphogenetic protein and/or another growth factor.

In some embodiments, the disclosure relates to pharmaceutical compositions comprising compounds disclosed herein, such as quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or a pharmaceutically acceptable salts thereof. In certain embodiments, the compositions further comprise a bone morphogenetic protein and/or another growth factor. In certain embodiments, the pharmaceutical composition is formulated to release over a 12 hour, 1 day, 3 day, 5 day, 7 day, two week, or one month period.

In certain embodiments, the disclosure relates to methods of preventing or treating a bone fracture comprising administering a pharmaceutical composition comprising compounds disclosed herein, such as quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or pharmaceutically acceptable salts thereof, to a subject at risk for, exhibiting symptoms of, or diagnosed with a bone fracture. In certain embodiments, the composition further comprises a bone morphogenetic protein and/or another growth factor. In certain embodiments, the administration is localized. In certain embodiments administration is achieved through oral delivery, intravenous delivery, parenteral delivery, intradermal delivery, percutaneous delivery, or subcutaneous delivery. In some embodiments, the method further comprises the step of exposing the bone fracture to pulsed electromagnetic fields. In further embodiments, the subject is diagnosed with a long bone shaft fracture such as a tibia or femur fracture corrected with intramedullary nail fixation.

In some embodiments, the disclosure relates to methods of preventing or treating a bone degenerative disease comprising administering a pharmaceutical composition comprising compounds disclosed herein, such as quinoline derivatives, 4-(phenoxy)-quinoline derivatives, N-phenylquinolin-4-amine derivatives, $N^2$-(phenyl)-$N^4$-(phenyl)

pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or pharmaceutically acceptable salts thereof, to a subject at risk for, exhibiting symptoms of, or diagnosed with a bone degenerative disease. In certain embodiments, the composition further comprises a bone morphogenetic protein and/or another growth factor. In certain embodiments, the administration is systemic or administration is achieved through oral delivery, intravenous delivery, parenteral delivery, intradermal delivery, percutaneous delivery, or subcutaneous delivery. In some embodiments, the disease is osteoporosis, osteitis deformans, bone metastasis, multiple myeloma, primary hyperparathyroidism, or osteogenesis imperfecta.

In some embodiments, the disclosure relates to methods for decreasing the time required to form new bone in the presence of a bone morphogenetic protein comprising co-administering at least one compound disclosed herein, such as quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof.

In some embodiments, the disclosure relates to a process for engineering bone tissue comprising combining a compound disclosed herein, such as quinoline derivatives, 4-(phenoxy)-quinoline derivatives, N-phenylquinolin-4-amine derivatives, $N^2$-(phenyl)-$N^4$-(phenyl) pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof, and optionally a bone morphogenetic protein with a cell selected from the group consisting of osteogenic cells, pluripotent stem cells, mesenchymal cells, and embryonic stem cells.

Typically the JAB1 blocker is used locally such as injection percutaneously at any bone formation site (fracture, spine fusion delayed a day or several days after surgery) etc. The JAB1 blocker may also be bound to a matrix or scaffold and delivered with growth factors, cells (MSCs or others), or on a dry carrier matrix to direct local bone formation in the shape of the carrier/scaffold.

Within certain embodiments, it is also contemplated that one or more of these compounds disclosed herein may be used alone or in combination with multiple compounds, with or without exogenous growth factors, and/or in combination with other agonists and promoting agents of the BMP pathway such as a noggin inhibitor, and/or a Smurf inhibitor.

DETAILED DISCUSSION

Figure 1:
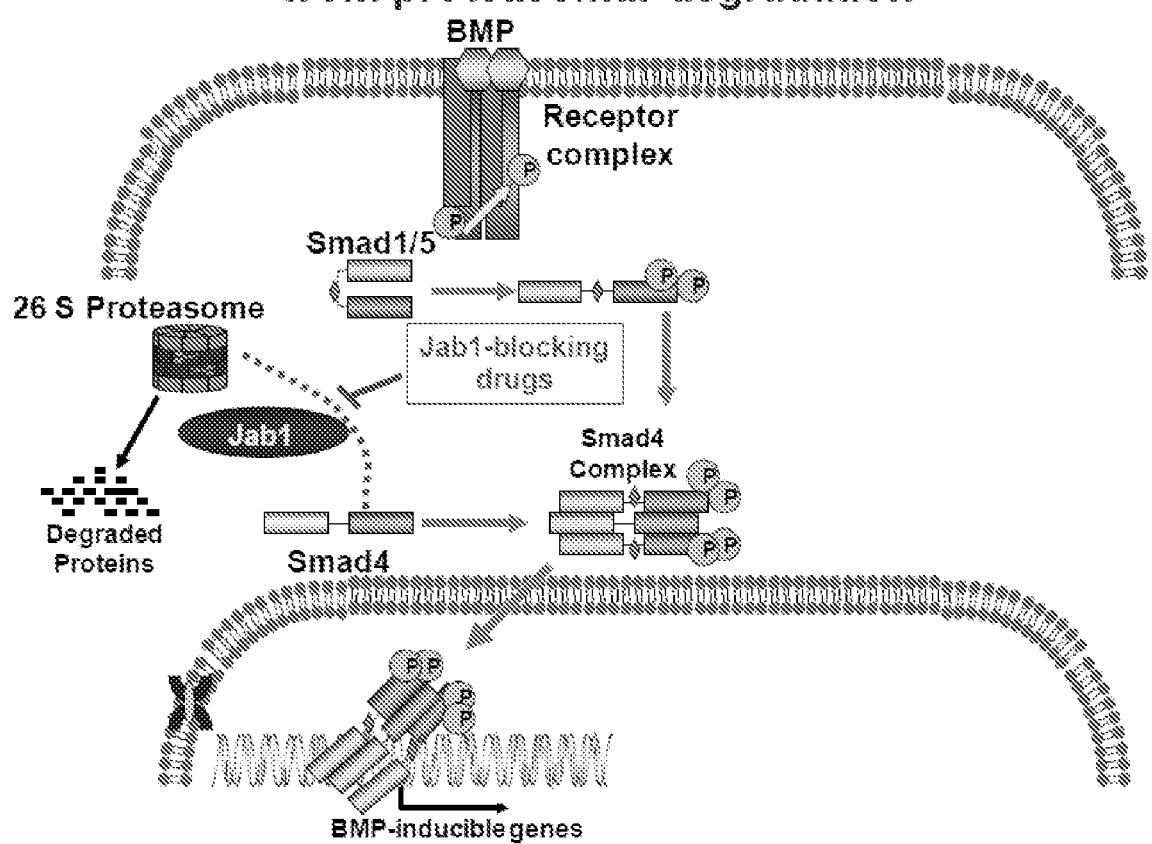
FIG. 1 shows a schematic representation of role of JAB1 in targeting Smad4 for proteasomal degradation.

Jun activation domain binding protein 1 (JAB1) is a regulator of the degradation of many regulatory proteins. JAB1 is also known as the 5th subunit of the COP signalosome exhibiting homology to the 26S proteasomal lid complex. JAB1 binds Smad5 and inhibits bone morphogenetic protein signaling. Haag & Aigner, ARTHRITIS & RHEUMATISM, 2006, 54(12), 3878-3884. JAB1 also antagonizes TGF-beta signaling by inducing Smad4 degradation. Wan et al., EMBO Rep., 2002, 3(2): 171-6. Modulating JAB1 interactions have the potential to either replace BMPs as a strategy to induce bone formation or to serve as a method to enhance the efficacy of BMPs. Human JAB1 is (SEQ ID NO: 6) 1 MAASGSGMAQ KTWELANNMQ EAQSIDEIYK YDKKQQQEIL AAKPWTKDHH YFKYCKISAL 61 ALLKMVMHAR SGGNLEVMGL MLGKVDGETM IIMDSFALPV EGTETRVNAQ AAAYEYMAAY 121 IENAKQVGRL ENAIGWYHSH PGYGCWLSGI DVSTQMLNQQ FQEPFVAVVI DPTRTISAGK 181 VNLGAFRTYP KGYKPPDEGP SEYQTIPLNK IEDFGVHCKQ YYALEVSYFK SSLDRKLLEL 241 LWNKYWVNTL SSSSLLTNAD YTTGQVFDLS EKLEQSEAQL GRGSFMLGLE THDRKSEDKL 301 AKATRDSCKT TIEAIHGLMS QVIKDKLFNQ INIS.

It is believed that the physiological presence of JAB1 blockers increases levels of Smad4 and increases responsiveness of BMPs or TGF-beta to promote bone and cartilage formation. Through in silico evaluations and an in vitro screening process, it has been discovered that certain compounds disclosed herein have the ability to enhance BMP activity.

Terms

"Ossification" refers to the process of laying down new bone by cells called osteoblasts. The term includes the growth in healing bone fractures treated by cast or by open reduction and stabilization by metal plate and screws. Ossification may also result in the formation of bone tissue in an extraskeletal location.

The term "bone morphogenetic protein" or "BMP" refers to any one of the family of growth factors or fragments thereof with the ability to induce the formation of bone and/or cartilage. The BMP receptors are typically serine-threonine kinases. It is not intended that BMP refer to any particular protein sequence and may or may not have certain glycosylation patterns attached thereto provided that the molecule has sufficient structural homology to any one of the known BMPs described below and retains some functional ability to promote bone growth, cartilage growth, or osteoblast differentiation. BMPs may be isolated from natural or non-natural sources, such as, but not limited to, recombinant or synthetic methods. References to BMPs generally or a specific BMP, e.g., BMP-2, includes recombinant or synthetically isolated versions unless otherwise provide for herein. Combinations of BMPs are contemplated. BMP-2 is known to induce bone and cartilage formation and play a role in osteoblast differentiation. BMP-3 is known to induce bone formation. BMP-4 is known to regulate the formation of teeth, limbs and bone from mesoderm and play a role in fracture repair. BMP-5 is known to function in cartilage development. BMP-6 is known to play a role in joint integrity and bone formation/repair. BMP-7 and BMP-9 are known to play a role in osteoblast differentiation. BMP-1 is a known metalloprotease that acts on procollagen I, II, and III and is involved in cartilage development.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "calcium phosphate(s)" refers to minerals containing calcium ions together with orthophosphates, metaphosphates or pyrophosphates and optionally hydroxide ions. Tricalcium phosphate is a calcium phosphate with formula $Ca_3(PO_4)_2$. The common mineral apatite has the basic formula $Ca_5(PO_4)_3X$, where X is a ion, typically a halogen or hydroxide ion, or a mixture. Hydroxyapatite refers to apatite where X is mainly hydroxide ion.

When used in reference to compound(s) disclosed herein, "salts" refer to derivatives of the disclosed compound(s) where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n- pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—$CH_3$).

"Alkanoyl" refers to an alkyl as defined above attached through a carbonyl bridge (i.e., —(C═O)alkyl).

"Alkylsulfonyl" refers to an alkyl as defined above attached through a sulfonyl bridge (i.e., —S(═O)$_2$alkyl) such as mesyl and the like, and "Arylsulfonyl" refers to an aryl attached through a sulfonyl bridge (i.e., —S(═O)$_2$aryl).

"Alkylsulfamoyl" refers to an alkyl as defined above attached through a sulfamoyl bridge (i.e., —S(═O)$_2$NHalkyl), and an "Arylsulfamoyl" refers to an alkyl attached through a sulfamoyl bridge (i.e., —S(═O)$_2$NHaryl).

"Alkylsulfinyl" refers to an alkyl as defined above with the indicated number of carbon atoms attached through a sulfinyl bridge (i.e. —S(═O)alkyl).

The terms "halogen" and "halo" refer to fluorine, chlorine, bromine, and iodine.

Compounds

Compounds derivatives disclosed herein may be used for bone and cartilage growth and related applications. Derivatives of certain compounds are further exemplified below.

In certain embodiments, the 4-(phenoxy)-quinoline derivative has formula I,

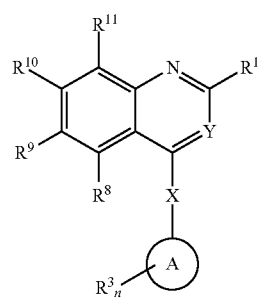

Formula I or salts thereof, wherein
A is a carbocyclyl, aryl, or heterocyclyl;
X is NH or O;
Y is N or $CR^2$;
n is 1, 2, 3, 4, or 5;
$R^3$ is the same or different at occurrence hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^3$ is optionally substituted with one or more, the same or different, $R^{12}$;
$R^1$, $R^2$, $R^8$, $R^9$, $R^{10}$, and a $R^{11}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfonyl, alkylsulfonyl, arylsulfonyl, carbocyclyl, aryl, or heterocyclyl, wherein each $R^1$, $R^2$, $R^8$, $R^9$, $R^{10}$, and $R^{11}$ are optionally substitutted with one or more, the same or different, $R^{12}$;
$R^{12}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfonyl, alkylsulfonyl, arylsulfonyl, carbocyclyl, aryl, or heterocyclyl, wherein $R^{12}$ is optionally substituted with one or more, the same or different, $R^{13}$; and
$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^2$ is hydrogen.
In certain embodiments, $R^3$ is selected from alkoxy, hydroxy, halogen, or alkyl.
In certain embodiments, $R^9$ is selected from alkoxy, hydroxy, halogen, or alkyl.
In certain embodiments, $R^{10}$ is selected from alkoxy, hydroxy, halogen, or alkyl:
In certain embodiments, the 4-(phenoxy)-quinoline derivative has formula IA,

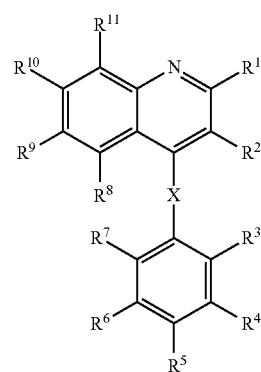

Formula IA or salts thereof, wherein
X is NH or O;
$R^1$, $R^2$, $R^3$, $R^4$, $R^5$, $R^6$, $R^7$, $R^8$, $R^9$, $R^{10}$, and $R^{11}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, and $R^{11}$ are optionally substituted with one or more, the same or different, $R^{12}$; or $R^4$ and $R^5$ and the attached atoms form a heterocyclyl optionally substituted with one or more, the same or different, $R^{12}$;

$R^{12}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^2$ is hydrogen.
In certain embodiments, $R^5$ is halogen.
In certain embodiments, $R^6$ is alkyl.
In certain embodiments, $R^9$ is selected from alkoxy.
In certain embodiments, $R^{19}$ is selected from alkoxy.
In certain embodiments, $R^1$, $R^2$, $R^3$, $R^4$, $R^7$, $R^8$, and $R^{11}$ are hydrogen.

In certain embodiments, the 4-(phenoxy)-quinoline derivative has formula IB,

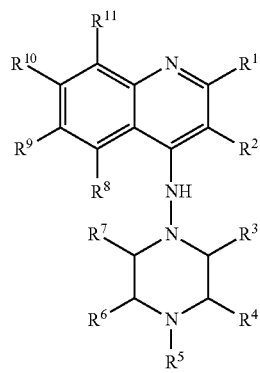

Formula IB r or salts thereof, wherein $R^1$, $R^2$, $R^3$, $R^4$, $R^5$, $R^6$, $R^7$, $R^8$, $R^9$, $R^{10}$, and $R^{11}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each. $R^1$, $R^2$, $R^3$, $R^4$, $R^5$, $R^6$, $R^7$, $R^8$, $R^9$, $R^{10}$, and $R^{11}$ are optionally substituted with one or more, the same or different, $R^{12}$;

$R^{12}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^2$ is hydrogen.
In certain embodiments, $R^4$ is alkyl.
In certain embodiments, $R^5$ is alkyl.
In certain embodiments, $R^{10}$ is halogen.
In certain embodiments, $R^1$, $R^2$, $R^3$, $R^6$, $R^7$, $R^8$, $R^9$, and $R^{11}$ are hydrogen.

In certain embodiments, the 3-(benzylidene)indolin-2-one derivative or 3-((indol-3-yl)methylene)indolin-2-one derivative is a compound of formula II,

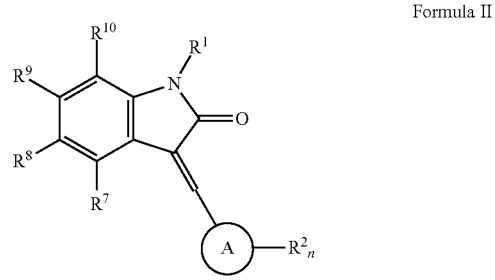

Formula II or salts thereof, wherein

A is a carbocyclyl, aryl, or heterocyclyl;

$R^1$, $R^7$, $R^8$, $R^9$, and $R^{10}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^7$, $R^8$, $R^9$, and $R^{10}$ are optionally substituted with one or more, the same or different, $R^{11}$;

$R^2$ is at each occurrence, the same or different, hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^2$ is optionally substituted with one or more, the same or different, $R^{11}$;

n is 0, 1, 2, 3, 4, or 5;

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N- diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the 3-(benzylidene)indolin-2-one derivative has formula IIA,

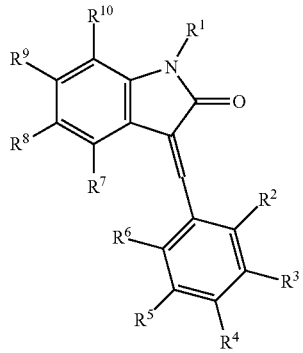

Formula IIA or salts thereof, wherein $R^1$, $R^2$, $R^3$, $R^4$, $R^5$, $R^6$, $R^7$, $R^8$, $R^9$, and $R^{10}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, and $R^{10}$ are optionally substituted with one or more, the same or different, $R^{11}$;

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is hydrogen.

In certain embodiments, $R^2$ is selected from alkoxy, hydroxy, halogen, and alkyl.

In certain embodiments, $R^4$ is selected from alkoxy, hydroxy, halogen, and alkyl.

In certain embodiments, $R^6$ is selected from alkoxy, hydroxy, halogen, and alkyl.

In certain embodiments, $R^9$ is selected from alkoxy, hydroxy, halogen, and alkyl.

In certain embodiments, $R^2$ is alkoxy.

In certain embodiments, $R^4$ is alkoxy.

In certain embodiments, $R^6$ is alkoxy.

In certain embodiments, $R^9$ is halogen.

In certain embodiments, $R^1$, $R^3$, $R^5$, $R^7$, $R^8$, and $R^{10}$ are hydrogen.

In certain embodiments, the $N^2$-(phenyl)-$N^4$-(phenyl)pyrimidine-2,4-diamine derivative has formula III,

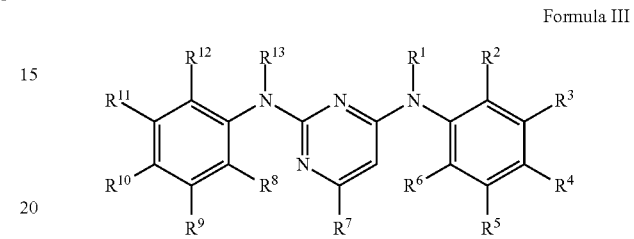

Formula III or salts thereof, wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, $R^6$, $R^7$, $R^8$, $R^9$, $R^{10}$, $R^{11}$, $R^{12}$, and $R^{13}$ are optionally substituted with one or more, the same or different, $R^{14}$;

$R^{14}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{15}$; and $R^{15}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ is selected from alkoxy, hydroxy, halogen, and alkyl.

In certain embodiments, $R^9$ is selected from alkoxy, hydroxy, halogen, and alkyl.

In certain embodiments, $R^{11}$ is selected from alkoxy, hydroxy, halogen, and alkyl.

In certain embodiments, $R^4$ is halogen.

In certain embodiments, $R^9$ is alkoxy.

In certain embodiments, $R^{11}$ is alkoxy.

In certain embodiments, $R^1$, $R^2$, $R^3$, $R^5$, $R^6$, $R^7$, $R^8$, $R^{10}$, $R^{12}$, and $R^{13}$ are hydrogen.

In certain embodiments, the 2-((phenylamino)methylene) malononitrile derivative or 2-benzylidenemalononitrile derivative is a compound of formula IV,

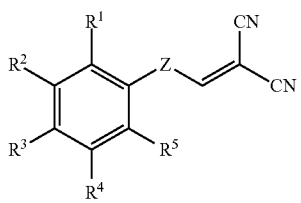

Formula IV or salts thereof, wherein

Z is NH or a direct bond between the phenyl ring and the alkenyl group;

$R^1$, $R^2$, $R^3$, $R^4$, and $R^5$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, and $R^5$ are optionally substituted with one or more, the same or different, $R^6$;

$R^6$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Processes of Preparing Compounds

Certain compounds disclosed herein may be prepared using corresponding starting materials as illustrated in the schemes below according to the procedures in Madrid et al. Bioorg. Med. Chem. Lett., 2005, 15, 1015-1018 and Hwang et al., J. Med. Chem., 2011, 54 (20), 7084-7093, or as appropriately modified. Both hereby incorporated by reference in their entirety. In certain embodiments, the disclosure contemplates methods of preparing compounds disclosed herein by mixing a phenol, aniline, or amine compound and a halogenated quinolone under conditions such that the compounds of formula I are formed. Similarly substituted-4-anilinoquinazolines may be prepared as provided in Felts et al., Bioorg Med Chem Lett., 2009, 19(23): 6623-6626 hereby incorporated by reference in its entirety.

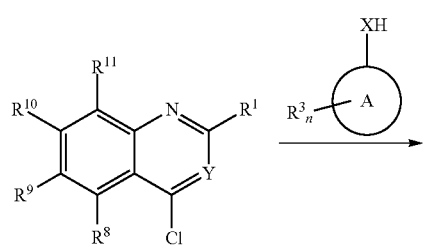

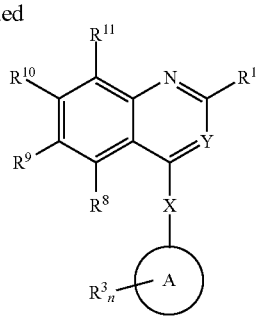

Certain compounds disclosed herein may be prepared using corresponding starting materials as illustrated in the schemes below according to the procedures in Quallich & Morrissey, Synthesis, 1993, 1, 51-53 and Ogawa et al., Chem. Pharm. Bull., 1988, 36, 2253-2258, or as appropriately modified. Both hereby incorporated by reference in their entirety. In certain embodiments, the disclosure contemplates methods of preparing compounds disclosed herein by mixing an aldehyde compound and an oxindole under conditions such that the compounds of formula II are formed.

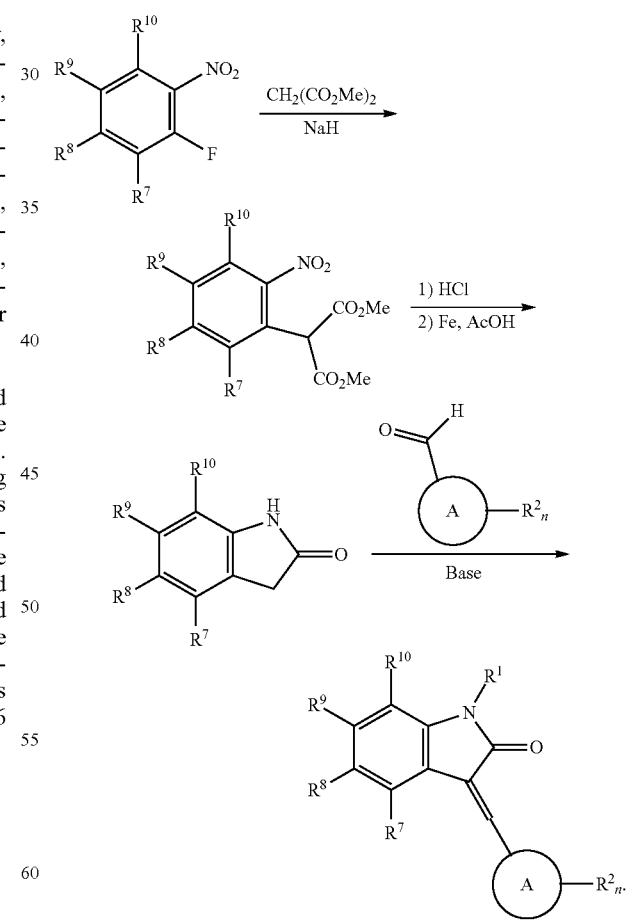

Certain compounds disclosed herein may be prepared using corresponding starting materials as illustrated in the schemes below according to the procedures in Hartung et al., Tetrahedron, 2006, 62, 10055-10064, Luo et al., Tetrahedron Letters, 2002, 43 5739-5742, and Ioannidis et al., J. Med. Chem., 2011, 54, 262-276, or as appropriately modified. All of these are hereby incorporated by reference in their entirety. In certain embodiments, the disclosure contemplates methods of preparing compounds disclosed herein by mixing an aniline compound and a halogenated pyrazole under conditions such that the compounds of formula Ill are formed.

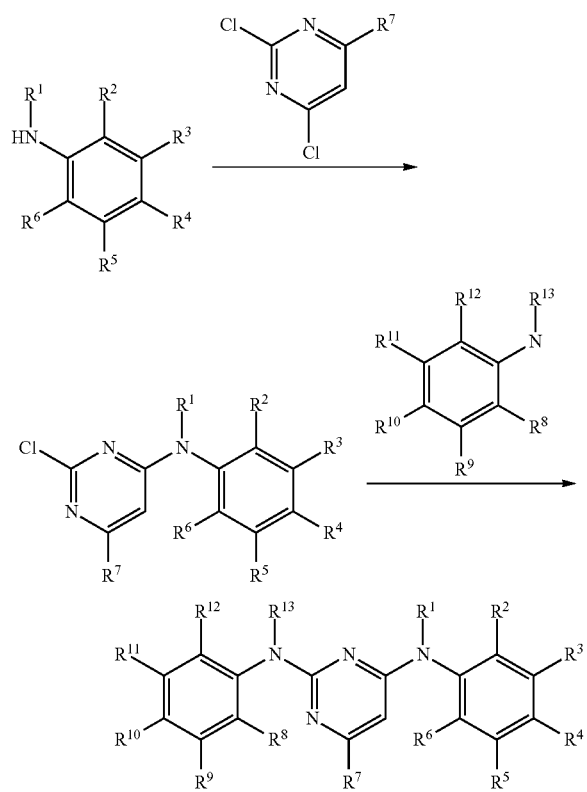

Certain compounds disclosed herein may be prepared using corresponding starting materials as illustrated in the schemes below according to the procedures in Zheng et al., J Med Chem., 2005, 48:7374-7388 and Beukers et al., J. Med. Chem. 2004, 47, 3707-3709, both hereby incorporated by reference in their entirety.

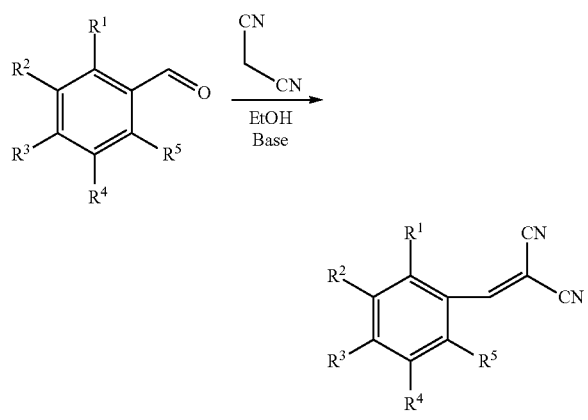

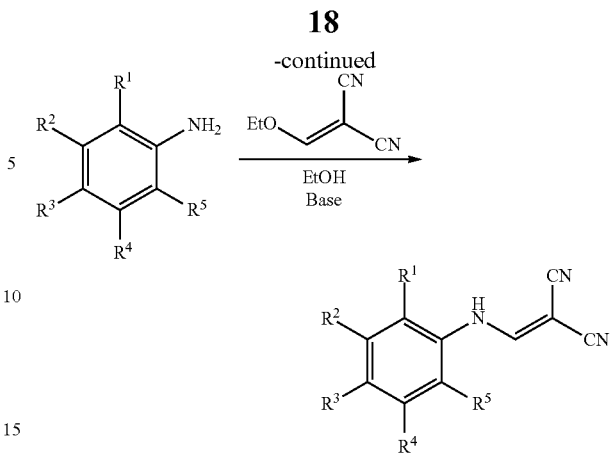

Growth Factors

In some embodiments, the disclosure relates to the combined use of growth factor(s) and compounds disclosed herein such as a quinoline derivative, 4-(phenoxy)-quinoline derivative, N-phenylquinolin-4-amine derivative, $N^2$-(phenyl)-$N^4$-(phenyl)pyrimidine-2,4-diamine derivative, 3-(benzylidene)indolin-2-one derivative, 2-((phenylamino)methylene)malononitrile derivative, 2-benzylidenemalononitrile derivative, N'-benzylidene-2-naphthohydrazide derivative, 3-((indol-3-yl)methylene)indolin-2-one derivative, or salts thereof and one or more growth factors in bone growth applications. Typically, the growth factor is a bone morphogenetic proteins (BMPs), including but not limited to, BMP-1, BMP-2, BMP-2A, BMP-2B, BMP-3, BMP-3b, BMP-4, BMP-5, BMP-6, BMP-7 (OP-1), BMP-8, BMP-8b, BMP-9, BMP-10, BMP-11, BMP-12, BMP-13, BMP-14, BMP-15. BMPs act through specific transmembrane receptors located on cell surface of the target cells.

Non-limiting examples of additional suitable growth factors include osteogenin, insulin-like growth factor (IGF)-1, IGF-II, TGF-beta1, TGF-beta2, TGF-beta3, TGF-beta4, TGF-beta5, osteoinductive factor (OIF), basic fibroblast growth factor (bFGF), acidic fibroblast growth factor (aFGF), platelet-derived growth factor (PDGF), vascular endothelial growth factor (VEGF), growth hormone (GH), growth and differentiation factors (GDF)-5 through 9, and osteogenic protein-1 (OP-1). The growth factors may be isolated' from synthetic methods, recombinant sources or may be purified from a biological sample. Preferably the growth factors are obtained from a recombinant technology and for clarity certain embodiments include rhBMP-2, rhBMP-4, rhBMP-6, rhBMP-7, and rhGDF-5, as disclosed, for example, in the U.S. Pat. Nos. 4,877,864; 5,013,649; 5,661,007; 5,688,678; 6,177,406; 6,432,919; 6,534,268, and 6,858,431, and in Wozney, J. M., et al. (1988) Science, 242(4885):1528-1534, all hereby incorporated by reference.

In a typical embodiment, a graft composition comprises a matrix, BMP-2, and a compound disclosed herein such as 4-(phenoxy)-quinoline derivatives, $N^2$-(phenyl)-$N^4$-(phenyl)pyrimidine-2,4-diamine derivatives, 3-(benzylidene)indolin-2-one derivative or salt thereof or combinations of other growth factors such as GDF-5. In one embodiment, the matrix contains an effective amount of a BMP-2 protein, an rhBMP-2 protein, functional fragments thereof, or combinations thereof. For certain embodiments, the range of concentrations of BMP-2 may be about 1.0 to 4.0 mg/ml and GDF-5 concentrations may be 0.25 to 4.0 mg/ml. Although a graft matrix may be loaded during manufacturing, it is typically loaded just prior to implantation.

The transcription of human BMP-2 is 396 amino acids in length, localized to chromosome 20p12. BMP-2 belongs to the transforming growth factor-beta (TGF-beta) superfamily. The human amino acid sequence BMP-2 is SEQ ID NO:1 shown below. Amino acids 38-268 are the TGF-beta propeptide domain, and 291-396 are the TGF-beta family N-terminal domain. Amino acids 283-396 are the mature peptide. The mature form of BMP-2 contains four potential N-linked glycosylation sites per polypeptide chain, and four potential disulfide bridges. (SEQ ID NO: 1) I MVAGTRCLLA LLLPQVLLGG AAGLVPELGR RKFAAASSGR PSSQPSDEVL SEFELRLLSM 61 FGLKQRPTPS RDAVVPPYML DLYRRHSGQP GSPAPDHRLE RAASRANTVR SFHHEESLEE 121 LPETSGKTTR RFFFNLSSIP TEEFITSAEL QVFREQMQDA LGNNSSFHHR INIYEIIKPA 181 TANSKFPVTR LLDTRLVNQN ASRWESFDVT PAVMRWTAQG HANHGFVVEV AHLEEKQGVS 241 KRHVRISRSL HQDEHSWSQI RPLLVTFGHD GKGHPLHKRE KRQAKHKQRK RLKSSCK-RHP 301 LYVDFSDVGW NDWIVAPPGY HAFYCHGECP FPLADHLNST NHAIVQTLVN SVNSKIPKAC 361 CVPTELSAIS MLYLDENEKV VLKNYQDMVV EGCGCR.

In one embodiment, bone morphogenetic protein includes one of the following synthetic peptide fragments of BMP-2: (SEQ ID NO: 2) KIPKASSVPTELSAISTLYLDDD, (SEQ ID NO: 3) CCCCDDDSKIPKASSVPTELSAISTLYL, (SEQ ID NO: 4) $C_{16}H_{31}O$—NH— CCCCGGG-SKIPKASSVPTELSAISTLYL which may be synthesized by FMOC/tBu solid-phase peptide synthesis.

BMP-7 also belongs to the TGF-beta superfamily. It induces cartilage and bone formation. The amino acid sequence of BMP-7 is SEQ ID NO: 5. (SEQ ID NO: 5) 1 MHVRSLRAAA PHSFVALWAP LFLLRSALAD FSLDNEVHSS FIHRRLRSQE RREMQREILS 61 ILGLPHRPRP HLQGKHNSAP MFMLDLYNAM AVEEGGGPGG QGFSYPYKAV FSTQGPPLAS 121 LQDSHFLTDA DMVMSFVNLV EHDKEFFHPR YHHREFRFDL SKIPEGEAVT AAEFRIYKDY 181 IRERFDNETF RISVYQVLQE HLGRESDLFL LDSRTLWASE EGWLVFDITA TSNHWVVNPR 241 HNLGLQLSVE TLDGQSINPK LAGLIGRHGP QNKQPFMVAF FKATEVHFRS IRSTGSKQRS 301 QNRSKTPKNQ EALRMANVAE NSSSDQRQAC KKHELYVSFR 361 DLGWQDWIIA PEGYAAYYCE GECAFPLNSY MNATNHAIVQ TLVHFINPET VPKPCCAPTQ LNAISVLYFD DSSNVILKKY 421 RNNVVRACGC H. Amino acids 1-29 are a potential signal sequence; 30-431 are the prepropeptide, and 293-431 are the mature protein. The mature form of BMP-7 contains four potential N-linked glycosylation sites per polypeptide chain, and four potential disulfide bridges.

Graft Compositions

In some embodiments, the disclosure relates to graft compositions comprising growth factor(s) and a quinoline derivative, 4-(phenoxy)-quinoline derivative, N-phenylquinolin-4-amine derivative, $N^2$-(phenyl)-$N^4$-(phenyl)pyrimidine-2,4-diamine derivative, 3-(benzylidene)indolin-2-one derivative, 2-((phenylamino)methylene)malononitrile derivative, 2-benzylidenemalononitrile derivative, N'-benzylidene-2-naphthohydrazide derivative, 3-((indol-3-yl) methylene)indolin-2-one derivative, or salts thereof. In certain embodiments, these compositions may be created from polymers, bone granules, and ceramics such as calcium phosphates (e.g. hydroxyapatite and tricalcium phosphate), bioglass, and calcium sulphate.

Bioglass refers to materials of $SiO_2$, $Na_2O$, CaO and $P_2O_5$ in specific proportions. The proportions differ from the traditional soda-lime glasses in lower amounts of silica (typically less than 60 mol %), higher amounts of sodium and calcium, and higher calcium/phosphorus ratio. A high ratio of calcium to phosphorus promotes formation of apatite crystals; calcium and silica ions may act as crystallization nuclei. Some formulations bind to soft tissues and bone, some only to bone, some do not form a bond at all and after implantation get encapsulated with non-adhering fibrous tissue, and others are completely absorbed overtime. Mixtures of 35-60 mol % $SiO_2$, 10-50 mol % CaO, and 5-40 mol% $Na_2O$ bond to bone and some formulations bond to soft tissues. Mixtures of >50 mol % $SiO_2$, <10 mol % CaO, <35 mol% $Na_2O$ typically intigrate within a month. Some CaO may be replaced with MgO and some $Na_2O$ may be replaced with $K_2O$. Some CaO may be replaced with $CaF_2$.

In some embodiments, the disclosure relates to a graft composition comprising growth factor(s) and compounds disclosed herein such as quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof and/or polysaccharides such as hyaluronate, cellulose or cellulose derivatives such as, but not limited to, hydroxypropyl cellulose, methyl cellulose, ethyl cellulose, and carboxymethyl cellulose. Typically, cellulose derivates are used in graft compositions that produce a paste or putty.

In some embodiments, the disclosure relates to bone graft compositions comprising a bone morphogenetic protein and quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salt thereof and a graft matrix. The matrix is typically a polymer designed to hold bone compatible salts, such as calcium phosphates, for replacement during bone growth. An example is a bovine Type I collagen embedded with biphasic calcium phosphate granules. Optionally, matrix compositions may also include one or more agents that support the formation, development and growth of new bone, and/or the remodeling thereof. Typical examples of compounds that function in, such a supportive manner include extracellular matrix-associated bone proteins such as alkaline phosphatase, osteocalcin, bone sialoprotein (BSP) and osteocalcin, phosphoprotein (SPP)-1, type I collagen, fibronectin, osteonectin, thrombospondin, matrix-gla-protein, SPARC, and osteopontin.

In certain embodiments, the graft matrix may be made up of a hydrogel polymer. Typically, a hydrogel is made-up of acrylate polymers and copolymers substituted with an abundance of hydrophilic groups, such as terminal hydroxy or carboxyl groups. In certain embodiments, the graft composition is biodegradable. In certain embodiments, the matrix comprises homopolymers and copolymers consisting of gylcolide and lactide. For certain embodiments, the graft composition comprises a matrix of hydroxyethylmethacrylate or hydroxymethylmethyacrylate polymers containing hydroxyapatite in a mineral content approximately that of human bone. Such a composition may also be made with crosslinkers comprising an ester, anhydride, orthoester, amide, or peptide bond. In some embodiments, crosslinkers contain the following polymers: polyethylene glycol (PEG), polylactic acid, polyglycolide or combinations thereof.

In certain embodiments, the graft composition may contain one or more antibiotics and/or anti-inflammatory agents. Suitable antibiotics include, without limitation, nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol or any combination thereof.

Suitable anti-inflammatory compounds include both steroidal and non-steroidal structures. Suitable non-limiting examples of steroidal anti-inflammatory compounds are corticosteroids such as hydrocortisone, cortisol, hydroxytriamcinolone, alpha-methyl dexamethasone, dexamethasonephosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene(fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds may also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

Bone Grafting Methods

Bone grafting is possible because bone tissue, unlike most other tissues, has the ability to regenerate if provided the space into which to grow with appropriate chemical signals. With regard to synthetic grafts, as native bone grows, it typically replaces most or all of the artificial graft material, resulting in an integrated region of new bone. However, with regard to certain embodiments of the disclosure, it is not intended that new bone must remove all artificial material. In addition, with regard to certain embodiments of the disclosure, it is not intended that graft location need contact any other bone of the skeletal system.

In certain embodiments, the disclosure relates to a method of forming bone comprising implanting a graft composition comprising a compound disclosed herein such as quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof, in a subject. In certain embodiments, the disclosure relates to methods of forming bone comprising implanting a graft composition comprising a bone morphogenetic protein and compound(s) disclosed herein, such as quinoline derivatives, 4-(phenoxy)-quinoline derivatives, N-phenylquinolin-4-amine derivatives, $N^2$-(phenyl)-$N^4$-(phenyl)pyrimidine-2,4-diamine derivatives, 3-(benzylidene)indolin-2-one derivatives, 2-((phenylamino)methylene)malononitrile derivatives, 2-benzylidenemalononitrile derivatives, N'-benzylidene-2-naphthohydrazide derivatives, 3-((indol-3-yl)methylene)indolin-2-one derivatives, or salts thereof, in a subject. The graft may be the result of a void created by surgical removal or created as a result of an attempt to correct a physical abnormality of a bone, such as but not limited to, cranial bones; frontal, parietal, temporal, occipital, sphenoid, ethmoid; facial bones; mandible, maxilla, palatine, zygomatic, nasal, lacrimal, vomer, inferior nasal conchae; shoulder girdle; scapula or shoulder blade, clavicle or collarbone; in the thorax; sternum, manubrium, gladiolus, and xiphoid process, ribs; in the vertebral column; cervical vertebrae, thoracic vertebrae; lumbar vertebrae; in the arms, humerus, radius, ulna; in the pelvis; coccyx; sacrum, hip bone (innominate bone or coxal bone); in the legs; femur, patella, tibia, and fibula. It is contemplated that the graft may be added for cosmetic purposes, e.g., cheek augmentation. In the case of a broken bone or removal of a bone during surgery, it may be desirable to secure movement of bone structure with a fixation system and remove the system after bone forms in the implanted graft.

With regard to prostheses, it may be desirable to grow bone between existing bone and an implanted device, or in preparation of an implanted device, such as in the case of a hip replacement, knee replacement, and dental implant, i.e., artificial tooth root used to support restorations that resemble a tooth or group of teeth.

In some embodiments, the disclosure relates to three-dimensional structures made of biocompatible and biodegradable bone graft materials in the shape of the bone infused with compositions disclosed herein to promote bone growth. Implants may be used to support a number of prostheses. A typical implant consists of a titanium device. In certain embodiments, the graft compositions disclosed herein contain implants.

With regard to a sinus augmentation or alveolar ridge augmentation, surgery may be performed as an outpatient under general anesthesia, oral conscious sedation, nitrous oxide sedation, intravenous sedation or under local anesthesia. Bone grafting is used in cases where there is a lack of adequate maxillary or mandibular bone in terms of depth or thickness. Sufficient bone is needed in three dimensions to securely integrate with the root-like implant. Improved bone height is important to assure ample anchorage of the root-like shape of the implant.

In a typical procedure, the clinician creates a large flap of the gingiva or gum to fully expose the bone at the graft site, performs one or several types of block and onlay grafts in and on existing bone, then installs a membrane designed to repel unwanted infection-causing bacteria. Then the mucosa is carefully sutured over the site. Together with a course of systemic antibiotics and topical antibacterial mouth rinses, the graft site is allowed to heal. The bone graft produces live vascular bone and is therefore suitable as a foundation for the dental implants.

In certain embodiments, the disclosure relates to methods of performing spinal fusion using compositions disclosed herein. Typically this procedure is used to eliminate the pain caused by abnormal motion of the vertebrae by immobilizing the vertebrae themselves. Spinal fusion is often done in the lumbar region of the spine, but the term is not intended to be limited to method of fusing lumbar vertebrae. Patients desiring spinal fusion may have neurological deficits or severe pain which has not responded to conservative treatment. Conditions where spinal fusion may be considered include, but are not limited to, degenerative disc disease, spinal disc herniation, discogenic pain, spinal tumor, vertebral fracture, scoliosis, kyphosis (i.e, Scheuermann's disease), spondylolisthesis, or spondylosis.

In certain embodiments, different methods of lumbar spinal fusion may be used in conjunction with each other. In one method, one places the bone graft between the transverse processes in the back of the spine. These vertebrae are fixed in place with screws and/or wire through the pedicles of each vertebra attaching to a metal rod on each side of the vertebrae. In another method, one places the bone graft between the vertebra in the area usually occupied by the intervertebral disc. In preparation for the spinal fusion, the disc is removed entirely. A device may be placed between the vertebrae to maintain spine alignment and disc height. The intervertebral device may be made from either plastic or titanium or other suitable material. The fusion then occurs between the endplates of the vertebrae. Using both types of fusion are contemplated.

Cartilage Repair

Cartilage is typically composed of chondroblasts, Type I and Type II collagen fibers, elastin fibers, and proteoglycans. Typical locations within the human body to find cartilage are the joints between bones, the ear, the nose, the elbow, the knee, the ankle, and the intervertebral discs. Cartilage can become damaged because of trauma or disease. In some embodiments, the disclosure relates to using compounds disclosed herein, derivatives, or salts thereof for the repair or regeneration of cartilage such as articular cartilage repair or regeneration or intervertebral disc cartilage repair or regeneration.

Articular cartilage repair is typically done to restore the cartilage on the surface of a bone, i.e., hyaline cartilage. Osteochondrial autografts or allografts may be performed. In certain embodiments, the disclosure contemplates methods of cartilage repair comprising transplanting sections of cartilage and/or bone to a location where cartilage and/or bone was removed and placing a compound disclosed herein, derivatives, or salts thereof about the surrounding area, e.g., by injections at the site of transplantation. Bone with its cartilage covering may be removed from the same or a different joint and replanted into the hole left from removing degraded bone and cartilage. The transplanted bone and cartilage are typically taken from areas of low stress.

In autologous chondrocyte implantation, cartilage cells are typically extracted arthroscopically from normal articular cartilage of the subject that is located in a nonload-bearing area, e.g., the intercondylar notch or the superior ridge of the femoral condyles, and the cells are replicated, in vitro, in the presence of growth factors. In certain embodiments, the disclosure relates to replicating cartilage cells comprising mixing hyaline cartilage and a compound disclosed herein, derivatives, or salts thereof, under conditions such that the cartilage cells replicate. Typically this is done by adding other growth factors to the cartilage replicating medium, e.g., cartilage-derived morphogenetic proteins and/or BMP proteins. The replicated chondrocytes are implanted to the desired area, e.g., injected about the site of the area for repair optionally in combination with either a membrane or a matrix comprising growth factors such as a CDMP, BMP protein or a compound disclosed herein.

Repair of articular cartilage may be performed by marrow stimulating procedures sometimes referred to as microfracture surgery. Damaged cartilage is typically ablated by, e.g., drilling or pounding, exposing the underlying bone—sometimes referred to as a microfracture. The subchondal bone typically generates a blood clot followed by cartilage regeneration. In some embodiments the disclosure relates to methods of generating cartilage by disrupting bone underlying articular cartilage and placing a compound disclosed herein about the area of disruption, e.g., by injecting compounds disclosed herein, derivatives, or salts thereof about the site of disrupted bone for the improved repair or regeneration of cartilage optionally in combination with a growth factor such as a CDMP and/or BMP protein. Alternatively it is contemplated that the compounds are administered to the subject in a pharmaceutical composition before, during or after the procedure. In another alternative, it is contemplated that a collagen matrix is implanted at the site of the exposed underlying bone to improve chondrogenic differentiation of mesenchymal stem cells. It is also contemplated that the subject may optionally be postoperative injected with compounds disclosed herein, hyaluronic acid, and/or mesenchymal stem cells, e.g., obtained from autologous peripheral blood progenitor cells.

Inflammation of the synovial membrane in a joint causes swelling and joint surface destruction. Removing excess fluid and material by a lavage or debridement frequently resolves arthritic knee inflammation and pain. In certain embodiments, the disclosure relates to the use of compounds disclosed herein, derivatives, or salts thereof before, during, or after a lavage or debridement inside a joint, e.g., arthroscopic lavage, arthroscopic debridement. In arthroscopic debridement, joint material or degenerative cartilage it typically removed by injecting a fluid and removing it with a vacuum.

An intervertebral disc (IVD) is found in between two vertebrae. The IVD contains different tissue types such as the annulus fibrosus (AF), the nucleus pulposus (NP), and end-plates. The AF is made up of mainly collagen type I. The amount of collagen type I decreases and collagen type II increase gradually nearer the NP which is mostly collagen type II dispersed within a proteoglycan-rich gelatinous matrix surrounding the NP.

Porous silk scaffolds may be used for a variety of tissue-engineering applications, such as the regeneration of bone and cartilage. Removal of sericin from silk reduces immunogenic responses. Silk may form a desired sponge-like structure by freeze-drying a silk solution. Bone marrow mesenchymal stem cells (BMSC) may be incorporated into porous silk scaffolds wrapped around a silicone NP substitute to form an artificial intervertebral disc. In certain embodiments, it is contemplated that compounds disclosed herein may be used to generate a matrix of annulus fibrosus by mixing with mesenchymal stem cells and growth factors. In certain embodiments, the disclosure contemplates implanting a fabricated intervertebral disc into a subject wherein the disc comprises annulus fibrosus tissue and placing a compound disclosed herein about the site of the implant location, e.g., by injection, optionally in combination with a growth factor such as a cartilage-derived morphogenetic protein (CDMP), e.g., CDMP-1 or CDMP-2, and/or bone morphogenetic proteins, e.g., BMP-7 or BMP-14. The fabricated disc may comprise a NP area with a hydrogel polymer/copolymer matrix or a collagen and/or hyaluronan and/or chondroitin-6-sulfate copolymer. A variety of stem cells, such as mesenchymal stem cells, synovium-derived stem cells (SDSCs), or notochord cells, may be used for rejuvenation of NP cells.

Therapeutic Applications

In some embodiments, the disclosure relates to pharmaceutical compositions comprising compounds disclosed herein for therapeutic applications. In some embodiments, the disclosure relates to methods of treating bone degenerative disorders, such as osteoporosis, osteitis deformans ("Paget's disease of bone"), bone metastasis (with or without hypercalcaemia), multiple myeloma, primary hyperparathyroidism, or osteogenesis imperfecta. Osteoporosis is a disease of bones that leads to an increased risk of fracture. In osteoporosis, the bone mineral density (BMD) is reduced, bone microarchitecture is disrupted, and the amount and variety of proteins in bone is altered. Osteoporosis is most common in women after menopause, when it is called postmenopausal osteoporosis, but may also develop in men, and may occur in anyone in the presence of particular hormonal disorders and other chronic diseases or as a result of medications, specifically glucocorticoids, when the disease is called steroid- or glucocorticoid-induced osteoporosis (SIOP or GIOP).

Osteoporotic fractures are those that occur in situations where healthy people would not normally break a bone; they are therefore regarded as fragility fractures. Typical fragility fractures occur in the vertebral column, rib, hip and wrist. The diagnosis of osteoporosis may be made using conventional radiography by measuring the bone mineral density (BMD).

In some embodiments, the disclosure relates to treating bone degenerative disorders by administering pharmaceutical composition described herein in combination with other agents, such as calcium carbonate and calcium citrate, vitamine D, cholecalciferol, 1,25-dihydroxycholecalciferol, calcitriol, estrogen, testosterone, raloxifene, pamidronate, neridronate, olpadronate, alendronate (Fosamax), ibandronate (Boniva), risedronate (Actonel), zoledronate (Zometa, Aclasta), etidronate (Didronel), clodronate (Bonefos, Loron), or tiludronate (Skelid).

In some embodiments, the disclosure relates to using compounds disclosed herein, derivatives, or salts thereof in the treatment of chondrodystrophies. Typically an effective amount of a pharmaceutical composition comprising the compound is administered to a subject diagnosed with, at risk of, or exhibiting symptoms of osteoarthritis, achondroplasia, costochondrits, relapsing polychondritis, or articular cartilage damage. The pharmaceutical compositions may provide pain relief or slow down the progression of damage delaying joint replacement (knee replacement) surgery.

In some embodiments, the disclosure relates to using compounds disclosed herein, derivatives, or salts thereof in the treatment of a degenerative intervertebral disc. Typically an effective amount of a pharmaceutical composition comprising the compound is administered to a subject diagnosed with, at risk of, or exhibiting symptoms of a degenerative disc. The compositions may be administered orally or injected directly into an intervertebral disc (IVD), e.g., into the annulus fibrosus (AF) and/or the nucleus pulposus (NP) optionally in combination with a growth factor such as a cartilage-derived morphogenetic protein (CDMP), e.g., CDMP-1 or CDMP-2, or a bone morphogenetic protein, e.g., BMP-7 or BMP-14.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When the compounds of the disclosure contain a hydrogen-donating heteroatom (e.g. NH), the disclsoure also covers salts and/or isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug may include a covalently bonded carrier which releases the active parent drug when administered to a mammalian subject. Prodrugs may be prepared by modifying functional groups present in the compounds in such a way that the modifications are cleaved, either in routine manipulation or in vivo, to the parent compounds. Prodrugs include, for example, compounds wherein a hydroxy group is bonded to any group that, when administered to a mammalian subject, cleaves to form a free hydroxy group. Examples of prodrugs include, but are not limited to, acetate, formate and benzoate derivatives of alcohol functional groups in the compounds. Methods of structuring a compound as prodrugs may be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxy group. It is well known that ester prodrugs are readily degraded in the body to release the corresponding alcohol. See e.g., Irnai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds may be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound may be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation may be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions may be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the invention as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the invention in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein or compound delivery systems. Proteins and/or compounds may be entrapped in the poly (lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One may attach poly(ethylene glycol) to proteins (PEGylation) to increase the in vivo half-life of circulating therapeutic proteins and decrease the chance of an immune response.

Experimental

Identification of a Motif in Smad4 and Other Natural Targets of JAB1 and Computational Modelling and Identification of Compounds that Potentiate BMP Signalling A motif in Smad4 and other natural targets of JAB I was identified that are predicted to interact with JAB I based on the MEME/MAST sequence analysis of several cellular signaling molecules that are known to interact with Jab-1 such as p27 (acyclin-dependent-kinase inhibitor), Leukocyte functional antigen-1, lutropin/choriogonadotropin receptor, c-jun, Smad4, p53 and psoriasins.

JAB1—interacting domain of Smad4 was modeled to computationally screen and select potential mimetic compounds that block JAB1 binding to Smad4. Compounds were screened in cell-based assays to select those that potentiate BMP signaling. Comprehensive datasets of JAB1 proteins were established by querying JAB/MPN domain of the human JAB1 sequence against non-redundant protein database (NR-DB) using PSI-BLAST until convergence ($16^{th}$ iteration). An E-value cutoff of 10-3 and bit score of 75 or above were used as search criteria. BLAST hits were searched against CDD, SMART and PFAM Databases using RPS-BLAST or HMMPFAM to investigate the protein domain composition of the hit sequences, most of the hits have shown single JAB_MPN or MOV4 domain. Further to remove redundancy CD-HIT was employed with applying 90% sequence identity cutoff. Putative JAB1 sequences were manually checked for presence of JAMM motif.

Figure 2A:
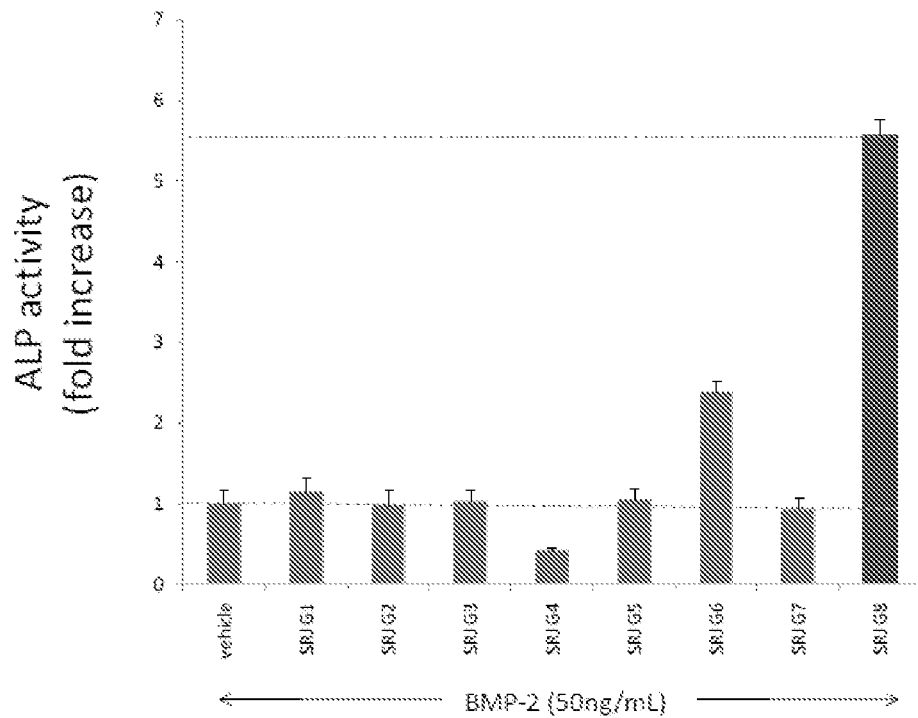
FIGS. 2A-C show data on the activity of G8, of the chemical formula 4-(4-bromo-3-methylphenoxy)-6,7-dimethoxyquinoline in an ALP assay and G6 of the chemical formula, 7-chloro-N-(4-(2,3-dimethylphenyl)piperazin-1-yl)quinolin-4-amine.
Figure 2B:
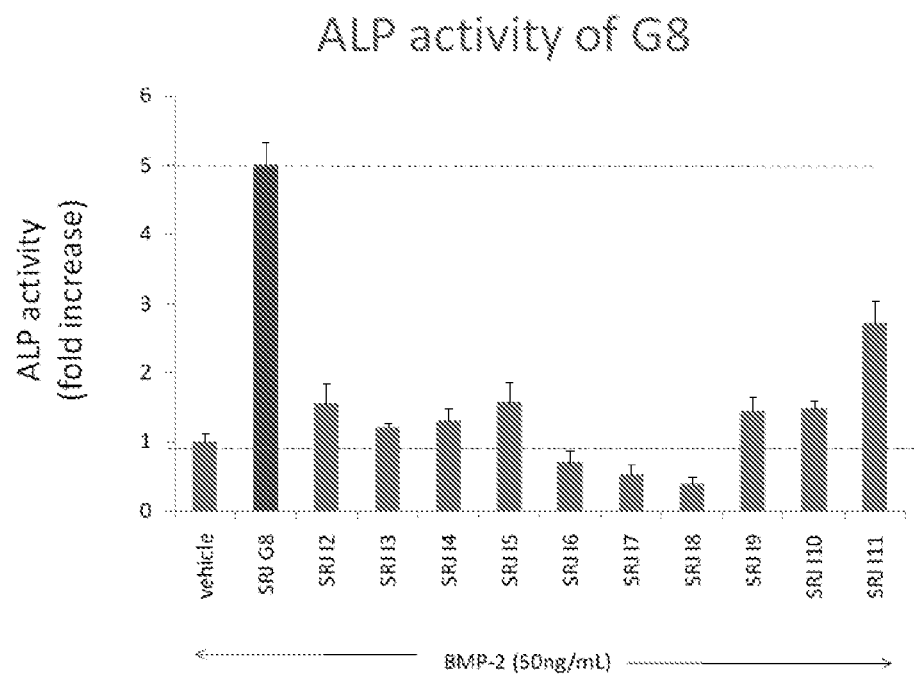
Figure 2C:
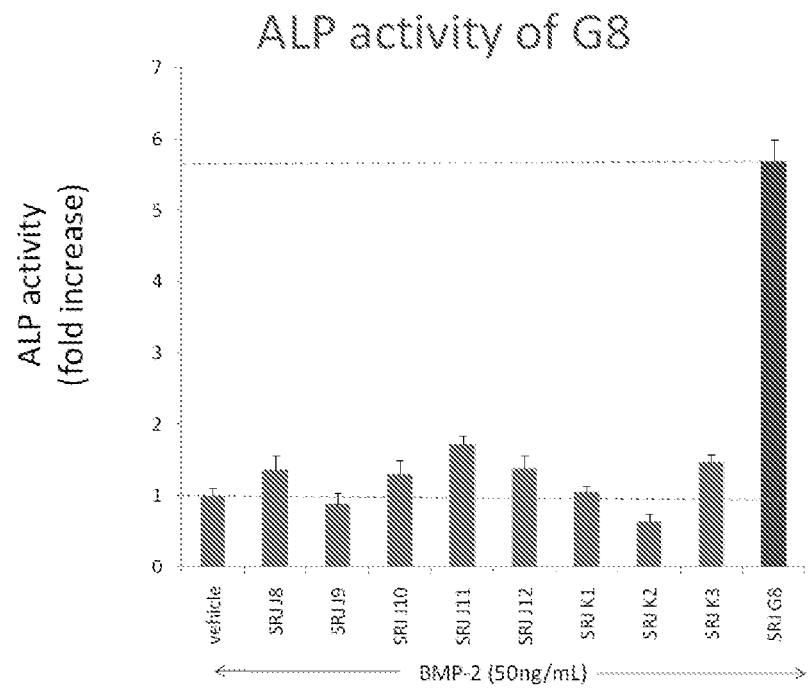
Figure 3A:
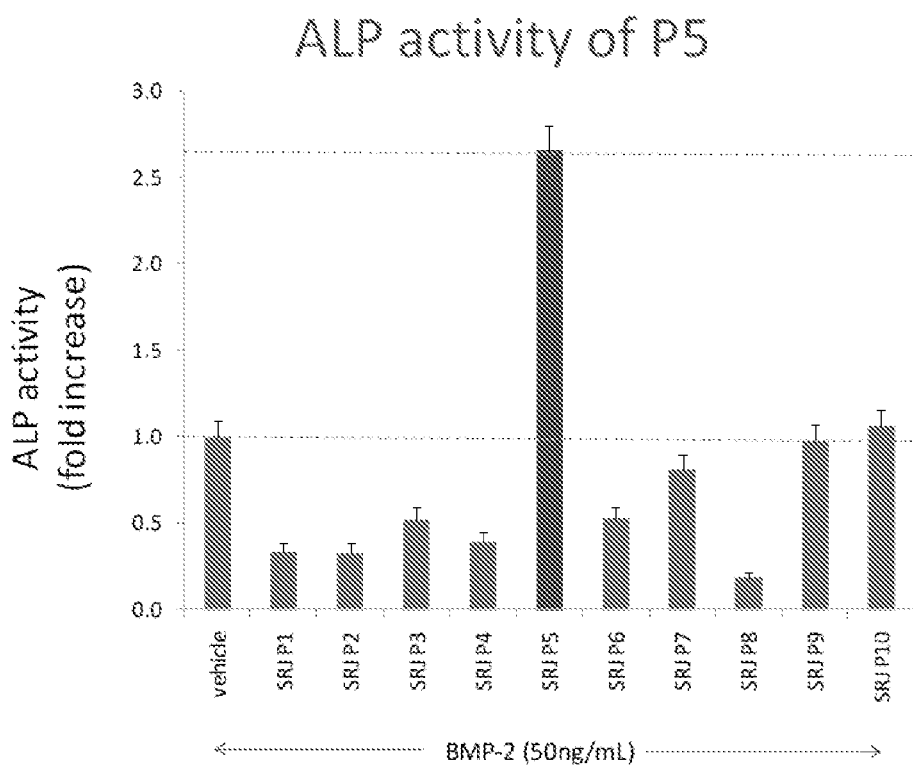
FIGS. 3A-C show data on the activity of P5, of the chemical formula $N^2$-(3,5-dimethoxyphenyl)-$N^4$-(4-fluorophenyl)pyrimidine-2,4-diamine, in an ALP assay.
Figure 3B:
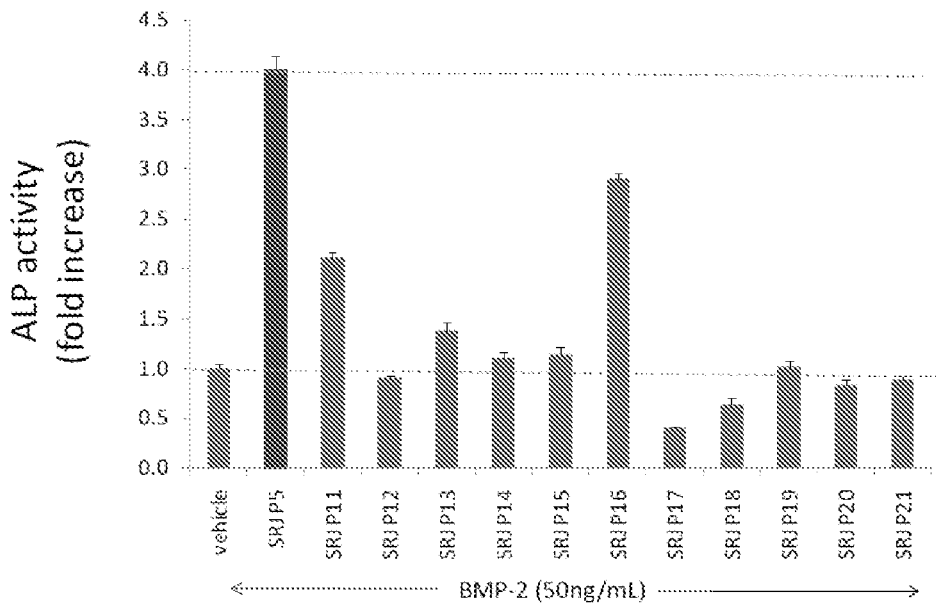
Figure 3C:
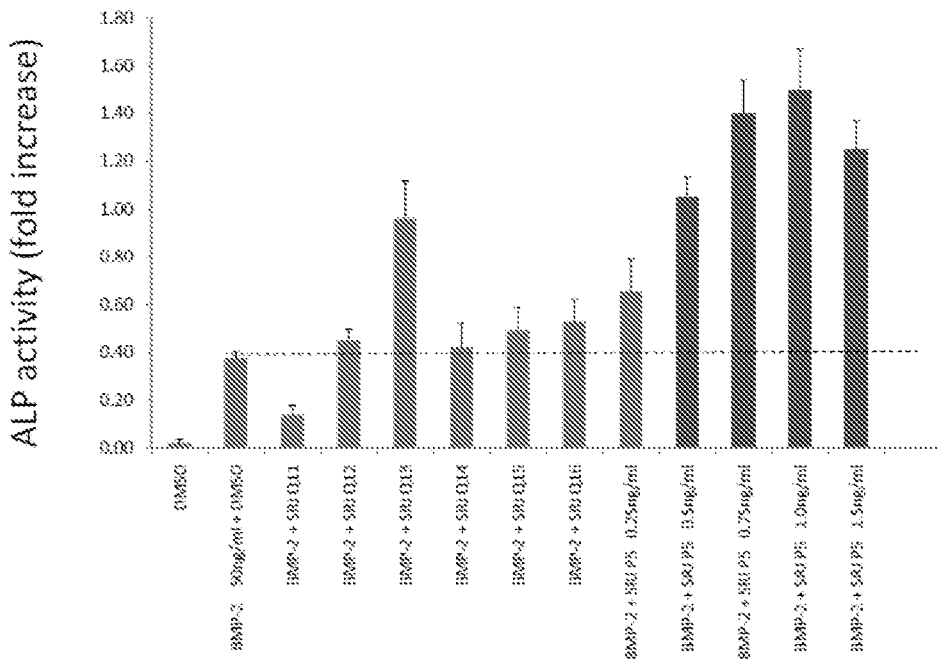
Figure 4:
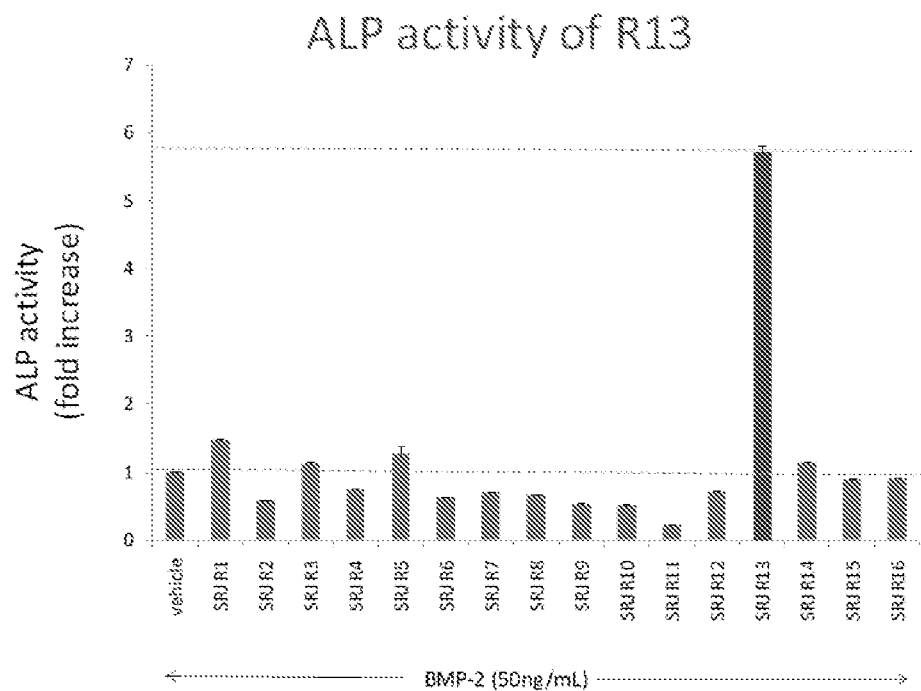
FIG. 4 shows data on the activity of R13, of the chemical formula 6-chloro-3-(2,4,6-trimethoxybenzylidene)indolin-2-one, in an ALP assay.
Figure 5:
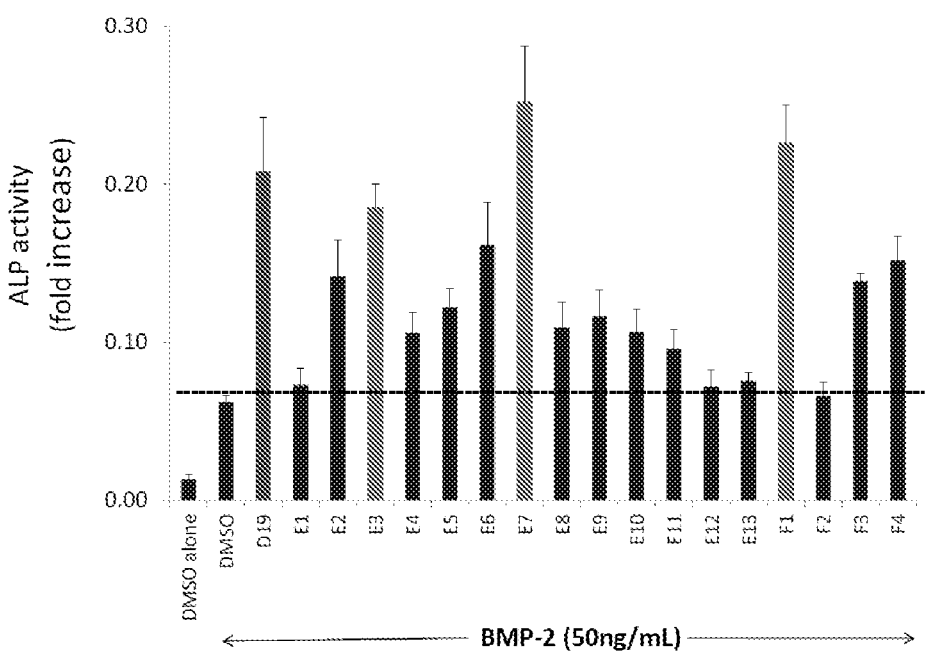
FIG. 5 shows data on the BMP potentiating activity of E3, E7, and F1. E3 is N-(3,5-difluorophenyl)-6,7-dimethoxyquinazolin-4-amine, E7 is N-(6,7-dimethoxyquinazolin-4-yl)benzo[d]thiazol-5-amine, and F1 is 2-(((4-bromophenyl)amino)methylene)malononitrile.
Figure 6:
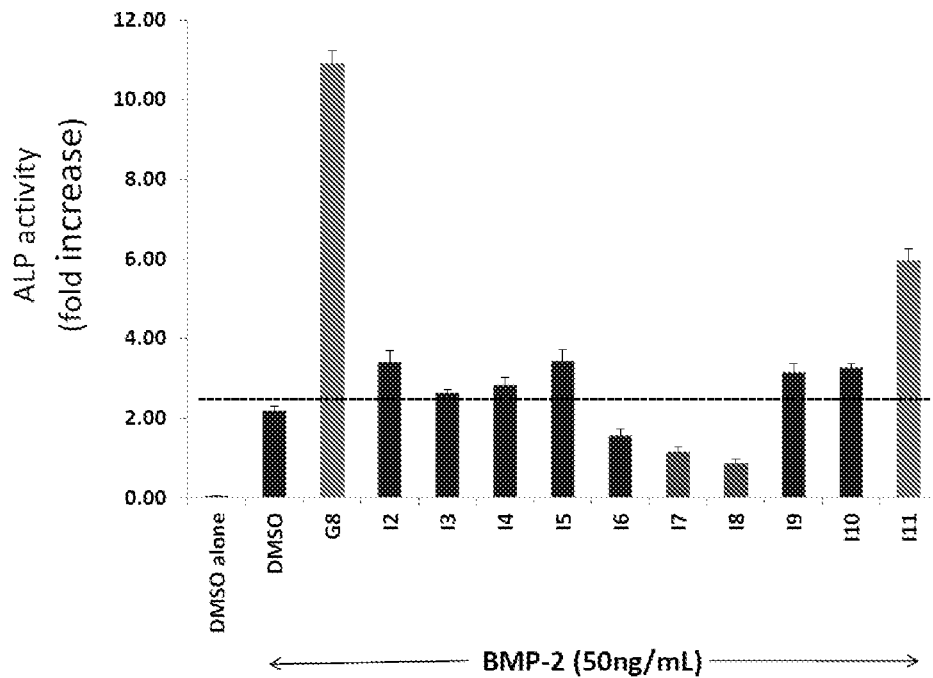
FIG. 6 shows data on the BMP potentiating activity of G8 and I11. I11 is N'-(3,5-dichloro-4-hydroxybenzylidene)-3-hydroxy-2-naphthohydrazide.
Figure 7:
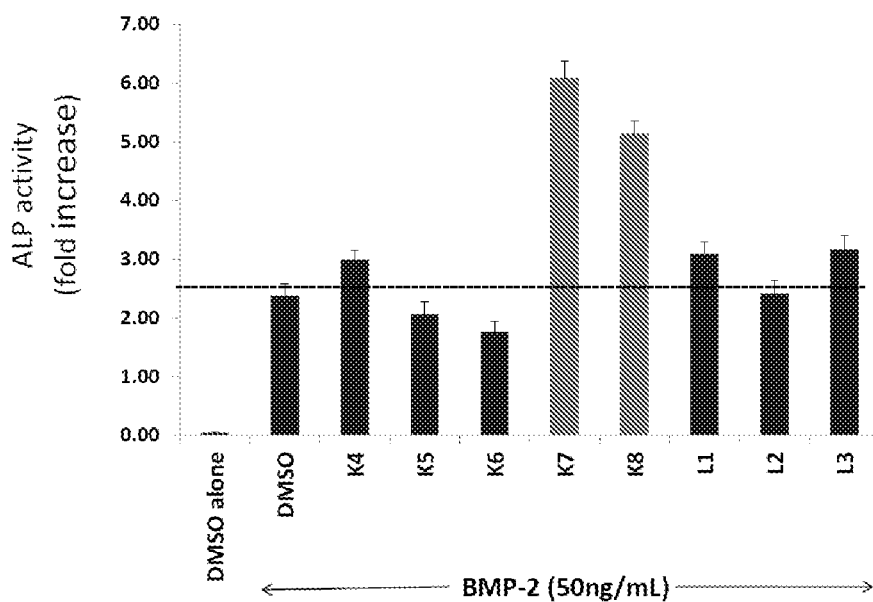
FIG. 7 shows data on the BMP potentiating activity of K7 and K8. K7 is 2-(3,4-dimethoxybenzylidene)malononitrile. K8 is 2-(2-hydroxy-5-methylbenzylidene)malononitrile.
Figure 8:
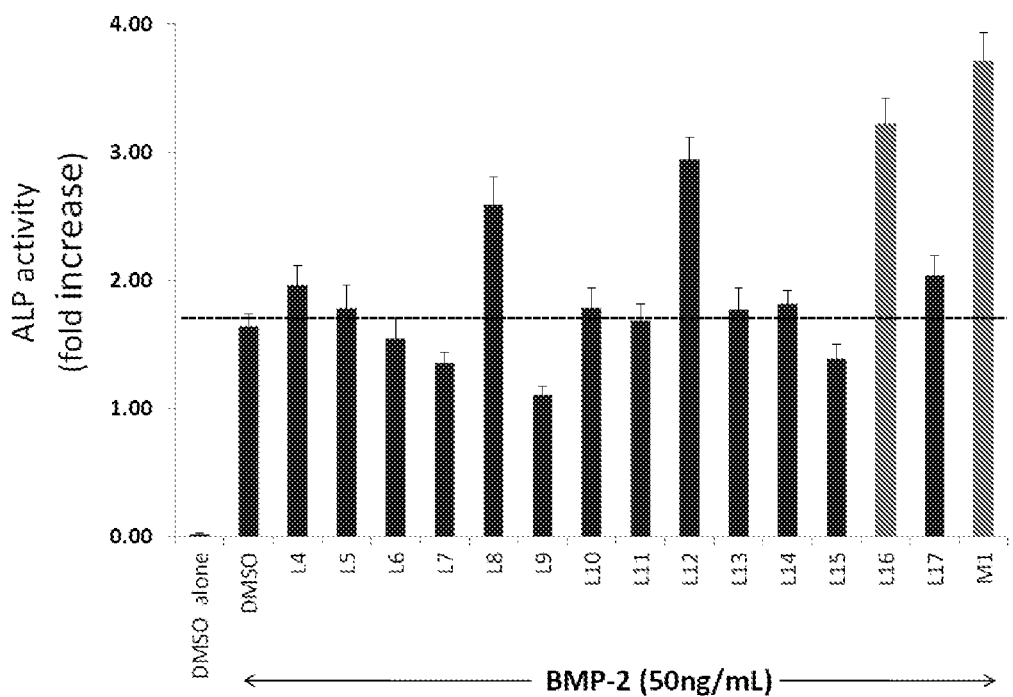
FIG. 8 shows data on the BMP potentiating activity of L16 and M1. L16 is 3-((indol-3-yl)methylene)-7-fluoroindolin-2-one and M1 is N-(3-chlorophenyl)-6,7-dimethoxyquinolin-4-amine.
Figure 9:
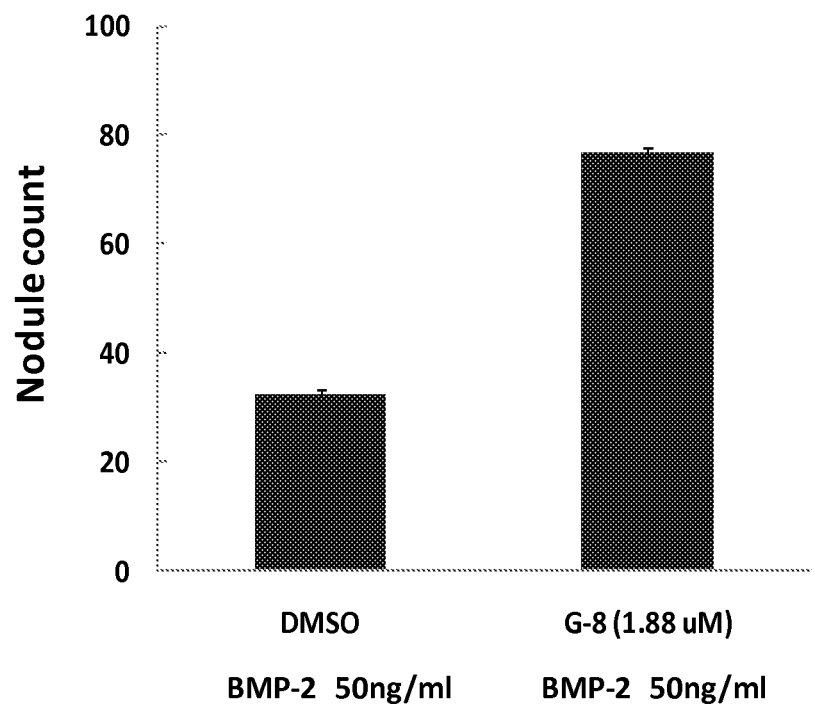
FIG. 9 shows data on the BMP potentiating activity of G8 in enhanced nodule formation in rat calvarial osteoblast cell cultures.

Amino acid sequence alignment of the regions of the rLHR, p27Kip1, and c-Jun that interact with JAB1 were identified. Using MEME (motif discovery tool) corresponding Jab-1 binding regions are detected in p53 and Smad4 (MH2 region). The consensus multiple sequence alignment file built for all five proteins is uploaded for MEME. Consensus JAB-1 interacting sequence in natural targets of JAB1 were identified. Identified JAB1 blockers were screened in a cell based assay (See FIG. 1-4). The compounds 4-(4-bromo-3-methylphenoxy)-6,7-dimethoxyquinoline $N^2$-(3,5-dimethoxyphenyl)-$N^4$-(4-fluorophenyl) pyrimidine-2,4-diamine and 6-chloro-3-(2,4,6-trimethoxybenzylidene)indolin-2-one were identified as improving ALP activity.

Cell Culture

Mouse C2Cl2 cells and Dulbecco's modified Eagle's medium (DMEM) were purchased from ATCC (Manassas, Va.). The non-heat inactivated fetal bovine serum (FBS) was purchased from HyClone Laboratories, Inc. (Logan, Utah). The C2Cl2 cells at passages 4 to 7 were subcultured in T-75 cm2 flasks in DMEM supplemented with 10% FBS at 37° C. in 5% CO2 with humidification. When the flasks reached 80% confluence, the cells were trypsinized and seeded in triplicate at 200,000 cells/well in a 6-well plate for quantitative real-time RT-PCR and alkaline phosphatase (ALP) assays or at 50,000 cells/well in a 12-well plate for the dual-luciferase reporter assay.

Alkaline Phosphatase (ALP) Assay

The C2Cl2 cells were plated at 200,000 cells/well in 6-well plates and grown overnight in DMEM containing 10% FBS. On day 2, the culture medium was replaced with DMEM containing 2% FBS and the cells were treated with various concentrations of the JAB1-interacting compound for 24 hours. On day 3, the medium was replaced with fresh DMEM containing 2% FBS and the cells were treated with 50 ng/ml of BMP-2 for 72 hours. The cells were washed with phosphate-buffered saline (PBS) and lysed by addition of lysis buffer (10 mM Tris-HCl pH 8.0, 1 mM MgCl2 and 0.5% Triton X-100). The cell lysates were centrifuged for 5 minutes at 13,000×g. The supernatant was removed and the aliquots were assayed for ALP activity and protein amount. The ALP activity was measured in triplicate using an ALP assay kit (Sigma-Aldrich, St. Louis, Mo.) in microtiter plates. The protein amount was determined with Bio-Rad protein assay reagent (Bio-Rad, Hercules, Calif.) using bovine serum albumin (BSA) as a standard. The ALP activity (nmoles of p-nitrophenol per ml) was normalized to the protein amount (nmoles of p-nitrophenol per µg).

Collagen Disc Implantation with Jabl-Blockers and BMP-2 in Rat Ectopic Model

Harlan athymic rats about 5-6 weeks of age were chest implanted with a collagen disc and doses of G8 and R13 in combination with BMP-2. After 4 weeks the rats were sacrificed and evaluated for bone growth. Certain doses showed improvement as summarized in the table below.

| Comp'd | Dose (mM) | BMP-2 Dose (ug) | Volume | Carrier | Results | Xray | Average |
|---|---|---|---|---|---|---|---|
| DMSO and #SRJ-G8 | n/a | 1.5 | 100 ul | collagen | Bone made (3 of 4) | 2+, 2+, 3+ | 1.75 |
|  | 2 | 1.5 | 100 ul | collagen | Bone made (4 of 4) | 2+, 3+, 4+, 5+ | 3.5 |
|  | 4 | 1.5 | 100 ul | collagen | Bone made (4 of 4) | 3+, 3+, 4+, 5+ | 3.75 |
|  | 6 | 1.5 | 100 ul | collagen | Bone made (3 of 4) | 4+, 4+, 4+ | 3 |
|  | 8 | 1.5 | 100 ul | collagen | Bone made (4 of 4) | 4+, 4+, 4+, 4+ | 4 |
|  | 11 | 1.5 | 100 ul | collagen | Bone made (1 of 4) | 5+ | 1.25 |
|  | 15 | 1.5 | 100 ul | collagen | Bone made (2 of 4) | 3+, 4+ | 1.75 |
|  | 19 | 1.5 | 100 ul | collagen | Bone made (1 of 4) | 3+ | 0.75 |
| DMSO and #SRJ-R13 | n/a | 1.5 | 100 ul | collagen | Bone made (2 of 4) | 1+, 2+ | 0.75 |
|  | 2 | 1.5 | 100 ul | collagen | Bone made (3 of 4) | 1+, 2+, 4+ | 1.75 |
|  | 4 | 1.5 | 100 ul | collagen | Bone made (4 of 4) | 1+, 2+, 3+, 3+ | 2.25 |
|  | 6 | 1.5 | 100 ul | collagen | No bone (0 of 4) |  |  |
|  | 8 | 1.5 | 100 ul | collagen | No bone (0 of 4) |  |  |
|  | 11 | 1.5 | 100 ul | collagen | No bone (0 of 4) |  |  |
|  | 15 | 1.5 | 100 ul | collagen | No bone (0 of 4) |  |  |
|  | 19 | 1.5 | 100 ul | collagen | No bone (0 of 4) |  |  |

What is claimed is:

1. A bone graft composition comprising a collagen matrix and a 4-(phenoxy)-quinoline derivative having formula IA,

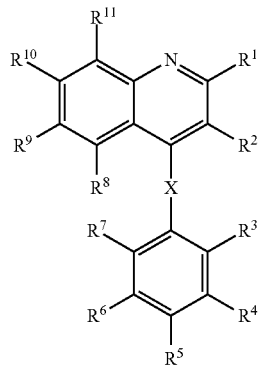

Formula IA or salts thereof, wherein

X is NH or O;

$R^1$, $R^2$, $R^3$, $R^4$, $R^5$, $R^6$, $R^7$, $R^8$, $R^9$, $R^{10}$ and $R^{11}$ are each the same or different hydrogen, alkyl, halogen, nitro, cyano, hydroxy, amino, mercapto, formyl, carboxy, alkanoyl, carbamoyl, alkoxy, alkylthio, alkylamino, or (alkyl)$_2$amino.

2. The bone graft composition of claim 1, wherein the 4-(phenoxy)-quinoline derivative, is covalently linked to the collagen matrix.

3. The graft of claim 1, further comprising a growth factor.

4. The graft of claim 3, wherein the growth factor is a bone morphogenetic protein.

5. The graft of claim 4, wherein the bone morphogenetic protein is BMP-2, BMP-7, BMP-6, or BMP-9.

6. The graft composition of claim 1, further comprising calcium phosphates.

7. The graft composition of claim 6, wherein said calcium phosphates are hydroxyapatite and tricalcium phosphate.

8. A kit comprising a 4-(phenoxy)-quinoline derivative having formula IA,

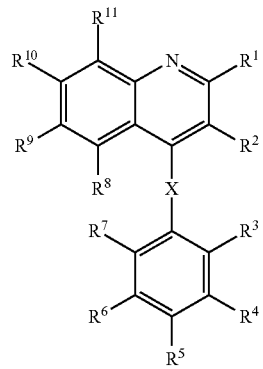

Formula IA or salts thereof, wherein

X is NH or O;

$R^1$, $R^2$, $R^3$, $R^4$, $R^5$, $R^6$, $R^7$, $R^8$, $R^9$, $R^{10}$ and $R^{11}$ are each the same or different hydrogen, alkyl, halogen, nitro, cyano, hydroxy, amino, mercapto, formyl, carboxy, alkanoyl, carbamoyl, alkoxy, alkylthio, alkylamino, or (alkyl)$_2$amino.

and a bone graft composition is selected from a collagen or hydrogel matrix and optionally a bone morphogenetic protein.

9. A bone graft composition comprising a hydrogel matrix and a 4-(phenoxy)-quinoline derivative having formula IA,

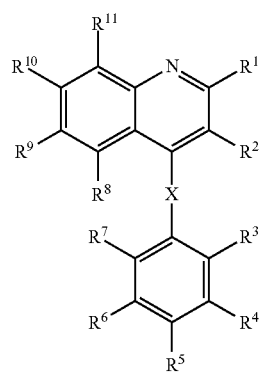

Formula IA or salts thereof, wherein
X is NH or O;
$R^1$, $R^2$, $R^3$, $R^4$, $R^5$, $R^6$, $R^7$, $R^8$, $R^9$, $R^{10}$ and $R^{11}$ are each the same or different hydrogen, alkyl, halogen, nitro, cyano, hydroxy, amino, mercapto, formyl, carboxy, alkanoyl, carbamoyl, alkoxy, alkylthio, alkylamino, or (alkyl)$_2$amino.

10. The graft of claim 9, further comprising a growth factor.

11. The graft of claim 10, wherein the growth factor is a bone morphogenetic protein.

12. The graft of claim 11, wherein the bone morphogenetic protein is BMP-2, BMP-7, BMP-6, or BMP-9.

13. The graft composition of claim 9, further comprising calcium phosphates.

14. The graft composition of claim 13, wherein said calcium phosphates are hydroxyapatite and tricalcium phosphate.

15. The graft of claim 9, wherein the 4-(phenoxy)-quinoline derivative is 4-(4-bromo-3-methylphenoxy)-6,7-dimethoxyquinoline or salts thereof.

16. The graft of claim 1, wherein the 4-(phenoxy)-quinoline derivative is 4-(4-bromo-3-methylphenoxy)-6,7-dimethoxyquinoline or salts thereof.

17. The kit of claim 8, wherein the 4-(phenoxy)-quinoline derivative is 4-(4-bromo-3-methylphenoxy)-6,7-dimethoxyquinoline or salts thereof.

18. The graft of claim 9, wherein $R^1$, $R^2$, $R^3$, $R^4$, $R^7$, $R^8$, and $R^{11}$ are hydrogen.

19. The graft of claim 1, wherein $R^1$, $R^2$, $R^3$, $R^4$, $R^7$, $R^8$, and $R^{11}$ are hydrogen.

20. The kit of claim 8, wherein $R^1$, $R^2$, $R^3$, $R^4$, $R^7$, $R^8$, and $R^{11}$ are hydrogen.

* * * * *